United States Patent
Byon et al.

(10) Patent No.: US 11,905,266 B2
(45) Date of Patent: Feb. 20, 2024

(54) COVALENT ORGANIC FRAMEWORK AND METHOD OF PREPARING THE SAME

(71) Applicant: Korea Advanced Institute of Science and Technology, Daejeon (KR)

(72) Inventors: Hye Ryung Byon, Daejeon (KR); Vikram Singh, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 97 days.

(21) Appl. No.: 17/643,720

(22) Filed: Dec. 10, 2021

(65) Prior Publication Data

US 2022/0194910 A1    Jun. 23, 2022

(30) Foreign Application Priority Data

Dec. 17, 2020 (KR) .......................... 10-2020-0177920
Nov. 22, 2021 (KR) .......................... 10-2021-0161169

(51) Int. Cl.
*C07D 277/66* (2006.01)
*H01M 4/60* (2006.01)
*H01M 4/02* (2006.01)

(52) U.S. Cl.
CPC ............ *C07D 277/66* (2013.01); *H01M 4/60* (2013.01); *H01M 2004/021* (2013.01)

(58) Field of Classification Search
CPC .. C07D 277/66; H01M 4/60; H01M 2004/021
See application file for complete search history.

(56) References Cited

U.S. PATENT DOCUMENTS 3,928,311 A * 12/1975 Fisher ................... C09B 44/103
    548/126
11,702,597 B2 * 7/2023 Kirsch ............... C09K 19/3068
    252/299.68

* cited by examiner

*Primary Examiner* — Helen Oi K Conley
(74) *Attorney, Agent, or Firm* — Knobbe, Martens, Olson & Bear, LLP

(57) ABSTRACT

A covalent organic framework and a method of preparing the same are disclosed. The covalent organic framework is used to produce an electrode material and includes a repeating unit represented by the following chemical formula:

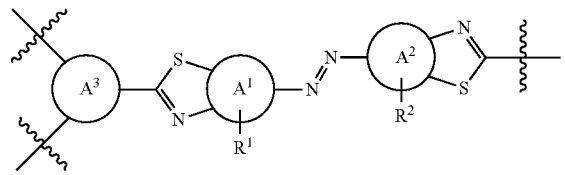

In the formula, $A^1$, $A^2$, and $A^3$ are the same or different, and are independently a monocyclic or polycyclic aromatic ring, and $R^1$ and $R^2$ are the same or different, and are independently selected from hydrogen, a functional group containing at least one nitrogen, phosphorus, or sulfur, an unsubstituted or substituted C1-C6 alkyl group, an unsubstituted or substituted C2-C6 alkenyl group, an unsubstituted or substituted C2-C6 alkynyl group, and an unsubstituted or substituted C1-C6 alkoxy group.

8 Claims, 18 Drawing Sheets

COVALENT ORGANIC FRAMEWORK AND METHOD OF PREPARING THE SAME

CROSS-REFERENCE TO RELATED APPLICATIONS

This application claims priority under 35 U.S.C. § 119 to Korean Patent Application No. 10-2020-0177920, filed on Dec. 17, 2020, and Korean Patent Application No. 10-2021-0161169, filed on Nov. 22, 2021 in the Korean Intellectual Property Office, the disclosure of which are incorporated herein by reference in their entirety.

TECHNICAL FIELD

The following disclosure relates to a covalent organic framework and a method of preparing the same, and more particularly, to a covalent organic framework for an electrode material and a method of preparing the same.

BACKGROUND

As a demand for the utilization of renewable energy such as solar, wind, and hydro energies is increased, the importance of development and utilization of an energy storage system (ESS) for storing electrical energy obtained by converting the renewable energy is highlighted. Currently, a lithium ion battery is widely used as the ESS in South Korea, but the lithium ion battery has high cost of cobalt, nickel, and the like used as an electrode material and a safety issue due to frequent fires of the lithium ion battery. The development of an inexpensive and safe battery is therefore desperately required.

SUMMARY

When an organic molecule is adjusted by adding redox-active functional groups, both redox potential and an electrode transfer rate may be adjusted, and thus, the organic molecule is expected to have a high application possibility when being applied as an electrode material of a battery. However, most monomolecular organic materials or polymers are inappropriate to be applied as an electrode material, due to their structural instability such as decomposition in an electrochemical reaction and low electrical conductivity.

A covalent organic framework (COF), which is a porous material formed by an organic molecule which forms a two-dimensional sheet by a covalent bond and grows into a three-dimensional shape by a n-n bond between sheets, is expected to form a stable molecular crystal to inhibit dissolution of an organic layer and form periodic mesopores to provide an effective ion transfer channel. Due to the characteristics, COF is under continuous research and development in various technical fields, but a covalent organic framework which has a stable chemical structure without being decomposed even during repeated charge and discharge as an electrode material has not been studied.

An embodiment of the present invention is directed to providing a covalent organic framework which has a stable chemical structure without being decomposed even during repeated charge and discharge of a battery.

Another embodiment of the present invention is directed to providing a covalent organic framework which has excellent cycle properties when applied as an electrode material and is capable of rapid charge and discharge.

In one general aspect, a covalent organic framework may include a repeating unit represented by the following Chemical Formula 1:

[Chemical Formula 1]

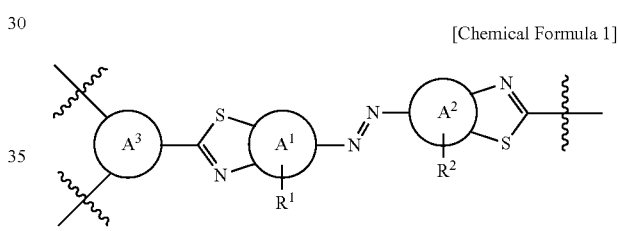

wherein $A^1$, $A^2$, and $A^3$ are the same as or different from one another, and are independently of one another a monocyclic or polycyclic aromatic ring, and $R^1$ and $R^2$ are the same as or different from each other, and are independently of each other any one selected from hydrogen, a functional group containing at least one nitrogen, phosphorus, or sulfur, an unsubstituted or substituted C1-C6 alkyl group, an unsubstituted or substituted C2-C6 alkenyl group, an unsubstituted or substituted C2-C6 alkynyl group, and an unsubstituted or substituted C1-C6 alkoxy group.

In addition, the covalent organic framework according to one embodiment may include a regular hexagonal structure having one side formed by the repeating unit of Chemical Formula 1 and being provided with a pore inside.

In addition, according to another embodiment, the pore may have a diameter of 1.0 to 8.0 nm.

In addition, the covalent organic framework according to another embodiment may include a structure represented by the following Chemical Formula 2:

[Chemical Formula 2]

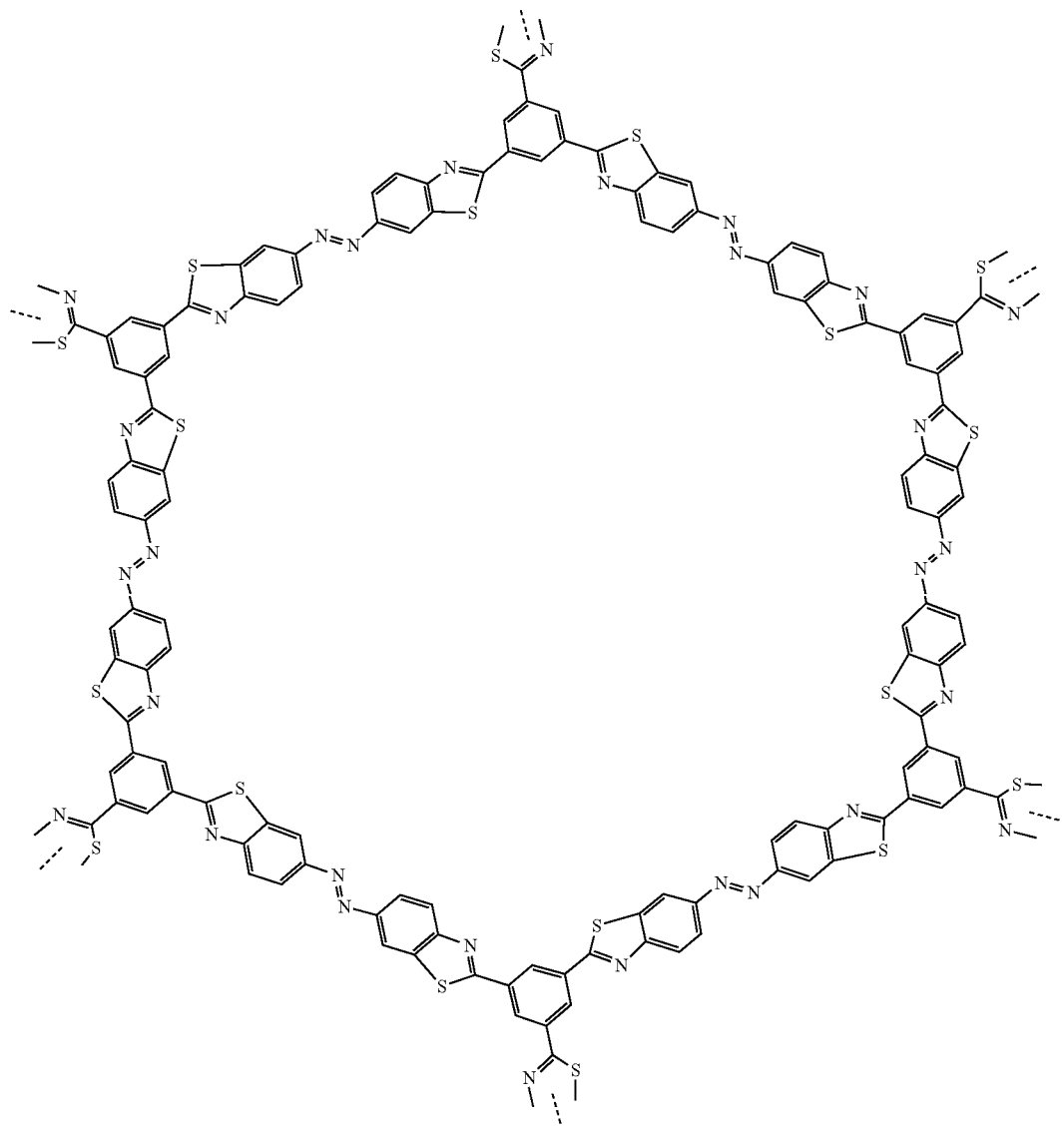

In addition, the covalent organic framework according to another embodiment of may include a two-dimensional sheet in which a repeating unit of Chemical Formula 1 is horizontally arranged.

In addition, the covalent organic framework according to another embodiment may include a three-dimensional mesoporous structure in which a plurality of the sheets are vertically arranged in any one stacking mode selected from a staggered stacking mode, an alternating stacking mode, a unidirectional stacking mode, a random stacking mode, and an eclipsed stacking mode.

In addition, according to another embodiment, a spacing between the vertically arranged sheets may be 1.0 nm or less.

In another general aspect, a method of preparing a covalent organic framework may include reacting a first monomer including a diamine represented by the following Chemical Formula 3 and a second monomer represented by Chemical Formula 4 to obtain a covalent organic framework intermediate including a repeating unit represented by the following Chemical Formula 5 and reacting the covalent organic framework intermediate and sulfur to obtain the covalent organic framework described above.

[Chemical Formula 3]

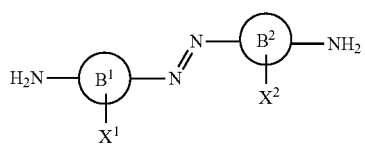

[Chemical Formula 4]

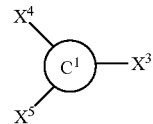

[Chemical Formula 5]

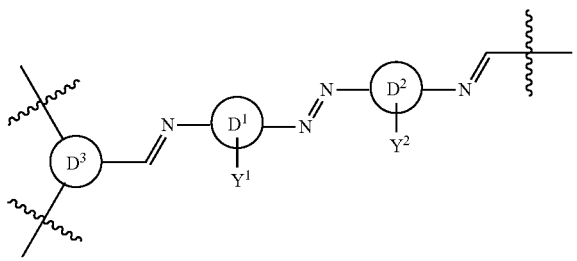

wherein in Chemical Formula 3,
$B^1$ and $B^2$ are the same as or different from each other, and are independently of each other a monocyclic or polycyclic aromatic ring, and
$X^1$ and $X^2$ are the same as or different from each other, and are independently of each other any one selected from hydrogen, a functional group containing at least one nitrogen, phosphorus, or sulfur, an unsubstituted or substituted C1-C6 alkyl group, an unsubstituted or substituted C2-C6 alkenyl group, an unsubstituted or substituted C2-C6 alkynyl group, and an unsubstituted or substituted C1-C6 alkoxy group,
in Chemical Formula 4,
$C^1$ is a monocyclic or polycyclic aromatic ring, and
$X^3$, $X^4$, and $X^5$ are the same as or different from one another, and are independently of one another a functional group including at least one of an aldehyde group, a ketone group, a carboxyl group, an ester group, and an amide group,
in Chemical Formula 5,
$D^1$, $D^2$, and $D^3$ are the same as or different from one another, and are independently of one another a monocyclic or polycyclic aromatic ring, and
$Y^1$ and $Y^2$ are the same as or different from each other, and are independently of each other any one selected from hydrogen, a functional group containing at least one nitrogen, phosphorus, or sulfur, an unsubstituted or substituted C1-C6 alkyl group, an unsubstituted or substituted C2-C6 alkenyl group, an unsubstituted or substituted C2-C6 alkynyl group, and an unsubstituted or substituted C1-C6 alkoxy group.

In addition, according to another embodiment, the diamine of Chemical Formula 3 may be 4,4'-azodianiline.

In addition, according to another embodiment, the Chemical Formula 4 may be 1,3,5-triformylbenzene.

In addition, according to another embodiment, a reaction molar ratio between the first monomer and the second monomer may be 1:0.5 to 1:1.5.

In addition, according another embodiment, the step of reacting the covalent organic framework intermediate and sulfur may include: providing the covalent organic framework intermediate and sulfur to a closed space in a vacuum, performing heating from 25° C. to 155° C. at a heating rate of 30 to 50° C./hr and at 155° C. for 3 hours, performing heating from 155° C. to 350° C. at a heating rate of 50 to 70° C./hr and then at 350° C. for 3 hours, and performing cooling to 25° C., Soxhlet extraction, and drying for 10 hours or more.

In addition, according to another embodiment, the Soxhlet extraction may include: using toluene to perform Soxhlet extraction for 24 hours and then using tetrahydrofuran to perform Soxhlet extraction for 24 hours.

In addition, the method of preparing a covalent organic framework according to another embodiment may have a yield of 50% or more.

In another general aspect, an electrode including the covalent organic framework described above is provided.

In still another general aspect, a battery including the electrode described above is provided.

According to one embodiment, cycle stability and fast charge characteristics may be secured by using a covalent organic framework including a thiazole-based linker as an electrode material.

According to another embodiment, a covalent organic framework capable of transferring two electrons at low potential may be provided by adopting an azo group as a redox core.

According to another, a covalent organic framework-based electrode having high crystallinity may be provided by using a topochemical-conversion method for forming n-conjugation in which a thiazole bond is extended and preserving an azo group.

The covalent organic framework according to one embodiment may have a porous channel having a pore diameter of 1.0 nm or more, so that lithium ions may easily pass through the inside of the framework, and thus, high ion conductivity may be secured.

When the covalent organic framework according to one embodiment forms an electrode, it is not decomposed even during repeated charge and discharge, so that cycle stability is excellent and charge and discharge characteristics are fast.

When an electrode is formed of the covalent organic framework according to one embodiment, the covalent organic framework may be applied to an organic matter-based light and flexible electrode, and thus, is excellent in the industrial effect.

DETAILED DESCRIPTION OF EMBODIMENTS

Figure 1A:
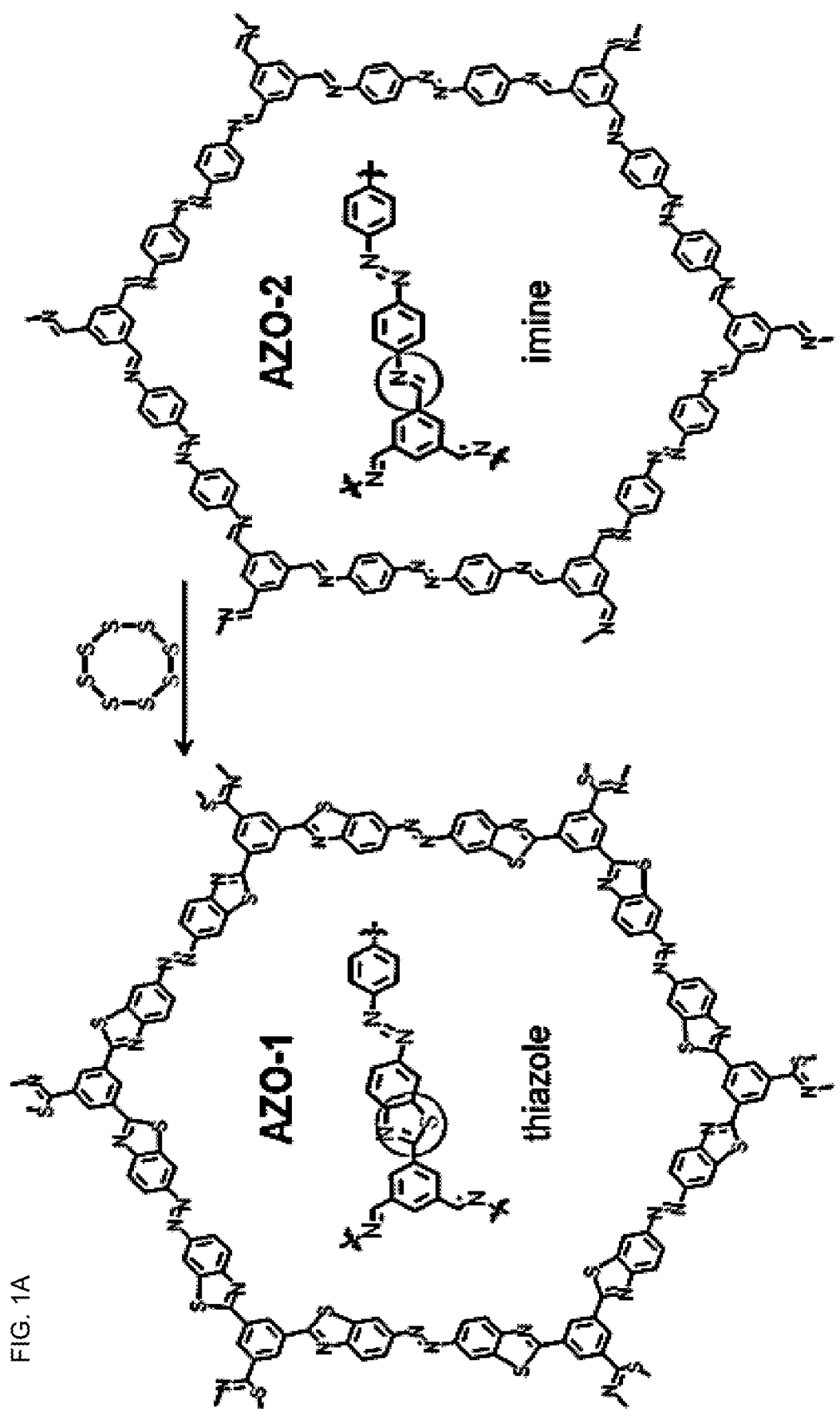
FIG. 1 is a drawing showing a preparation process of AZO-1 of Example 1, AZO-2 of Comparative Example 1, and AZO-3 of Comparative Example 2, and a pore diameter and an interlayer spacing of the prepared covalent organic frameworks.
Figure 1B:
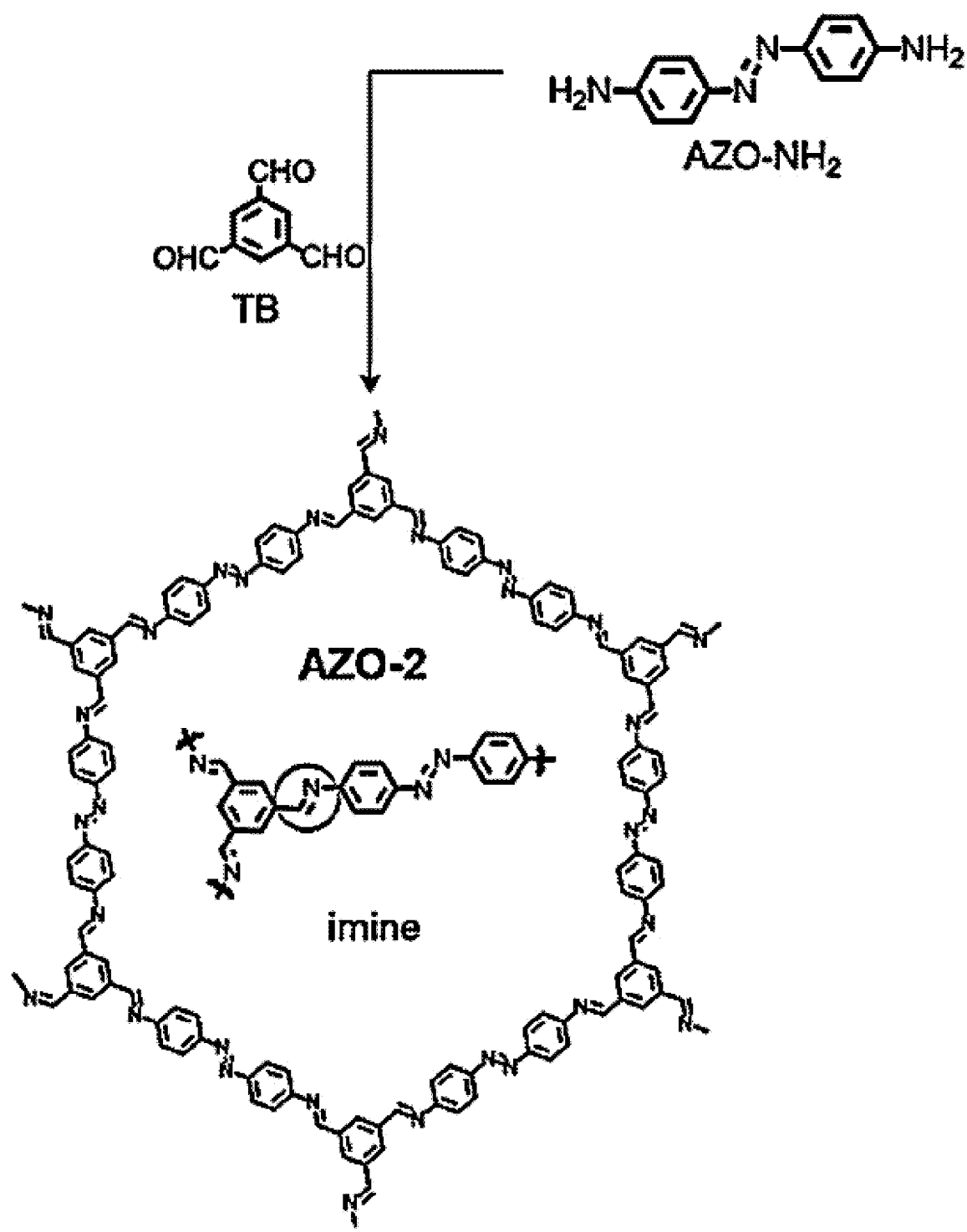
Figure 1C:
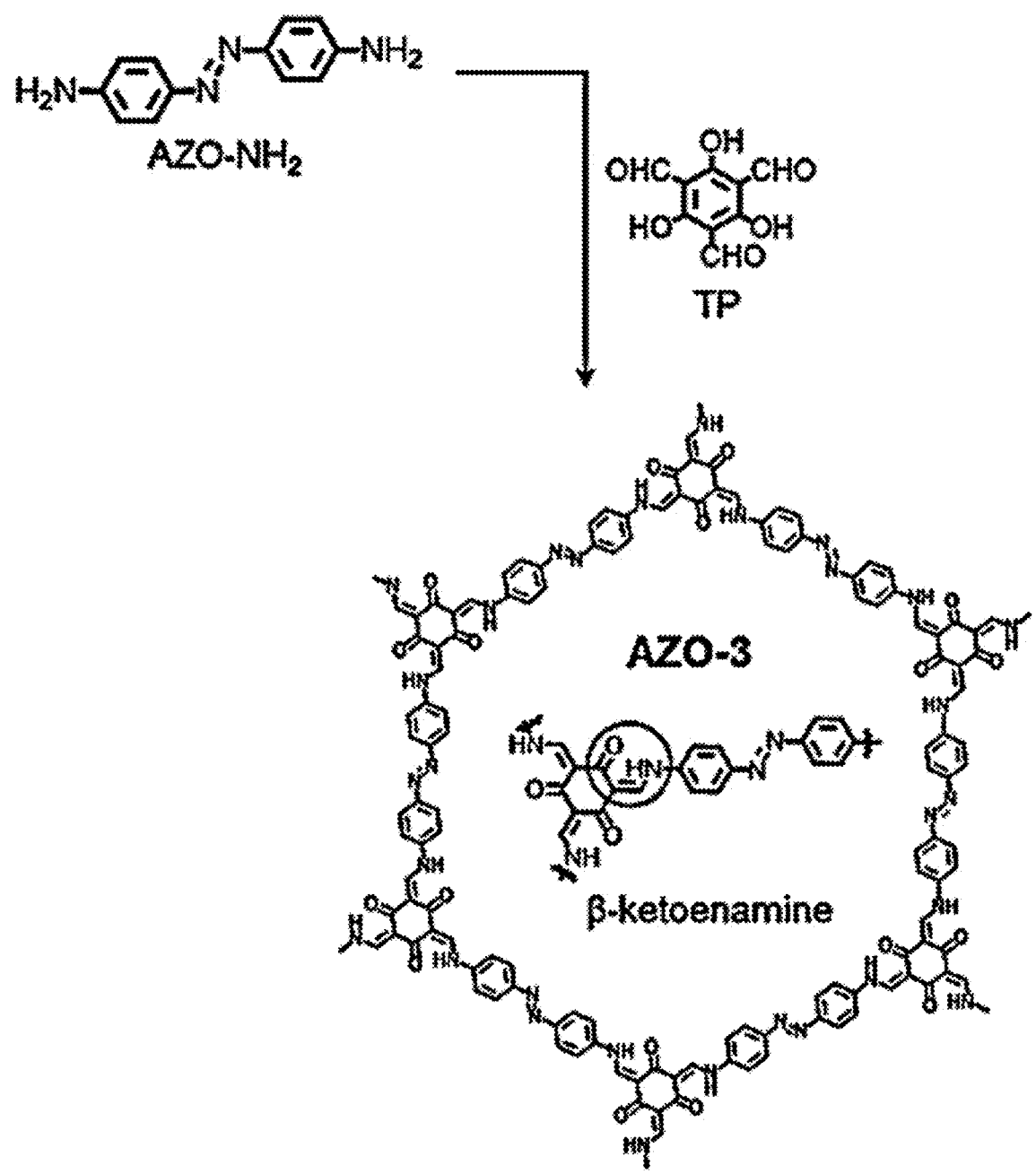
Figure 1D:
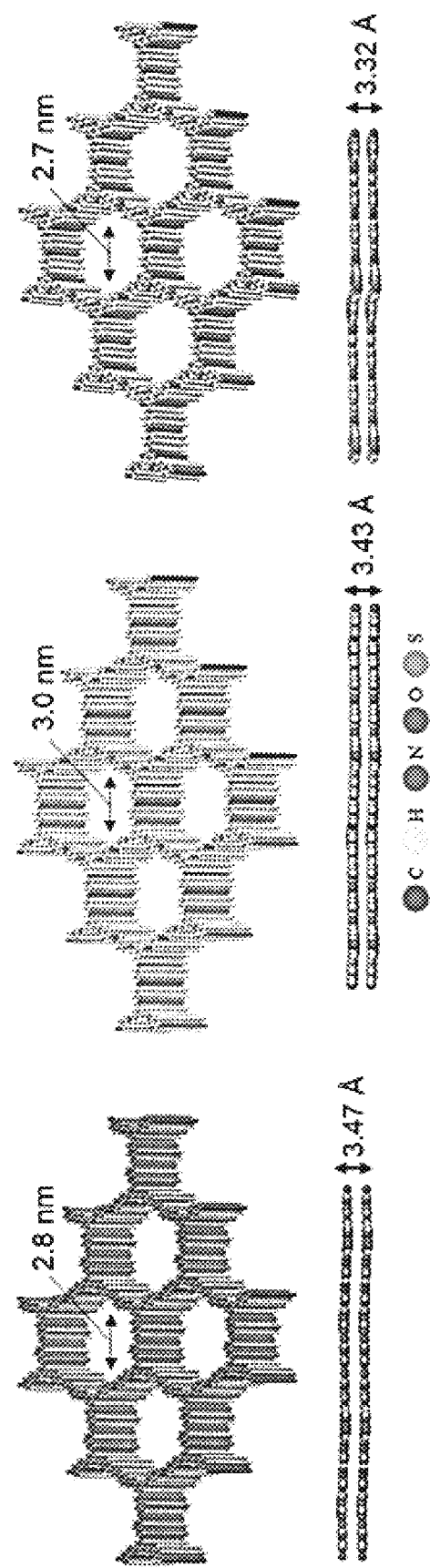

The terms used in the present application are used only for describing a specific example. Thus, for example, singular forms are intended to include plural forms, unless the singular forms should be clearly singular contextually. In addition, it should be noted that the terms such as "comprise" or "provided with" used in the present application are used for clearly indicating the presence of characteristics, steps, functions, constituent elements, or combinations thereof described in the specification, and are not used for precluding the presence of other characteristics, functions, constituent elements, or combinations thereof.

Meanwhile, unless otherwise defined, it is to be understood that all terms used in the specification have the same meaning as those commonly understood by those skilled in the art. Therefore, unless otherwise clearly defined, a specific term should not be interpreted in an excessively idealistic or formal meaning.

In addition, "about", "substantially", and the like in the present specification are used in the numerical value or in the meaning close to the numerical value when a unique manufacturing and material allowable error is suggested in the mentioned meaning, and are used for preventing the disclosure mentioning a correct or absolute numerical value for better understanding of the present invention from being unfairly used by an unconscientious infringer.

A covalent organic framework has been expected to be utilized in various electrode structures, when being made highly conductive and flexible for stabilizing a redox function. However, contrary to the common idea, a covalent organic framework-based electrode hardly satisfied the high capacity, cycle stability, and high-rate characteristics. This is presumed to be due to the lack of structural stability of the covalent organic framework, resulting in decomposition of the covalent organic framework to deteriorate battery performance.

A thiazole moiety was combined with an organic scaffold, thereby securing a n-conjugated and crystalline organic electrode to secure structural stability even during repeated charge and discharge. In addition, a covalent organic framework capable of rapid two-electron transfer in a single step was intended to be designed by utilizing an azo reactor.

The covalent organic framework according to one embodiment may include a repeating unit represented by the following Chemical Formula 1:

[Chemical Formula 1]

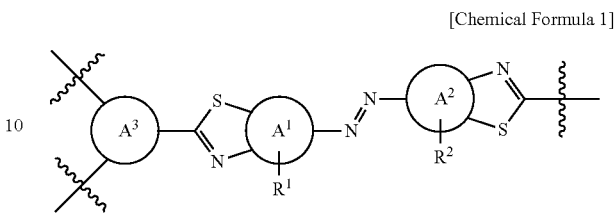

wherein $A^1$, $A^2$, and $A^3$ are the same as or different from one another, and are independently of one another a monocyclic or polycyclic aromatic ring, and $R^1$ and $R^2$ are the same as or different from each other, and are independently of each other any one selected from hydrogen, a functional group containing at least one nitrogen, phosphorus, or sulfur, an unsubstituted or substituted C1-C6 alkyl group, an unsubstituted or substituted C2-C6 alkenyl group, an unsubstituted or substituted C2-C6 alkynyl group, and an unsubstituted or substituted C1-C6 alkoxy group.

A monocyclic aromatic ring may be, for example, unsubstituted or substituted benzene or aromatic heterocyclic compound. However, the monocyclic aromatic ring of the present disclosure is not limited to the examples described above.

The polycyclic aromatic ring may be, for example, an unsubstituted or substituted bicyclic aromatic ring such as naphthalene and azulene; a tricyclic aromatic ring such as anthracene, phenanthrene, and fluorene; a tetracyclic aromatic ring such as tetracene and pyrene; or a combination thereof, or a polycyclic aromatic ring derived therefrom, and may contain one or more heterocycles. However, the polycyclic aromatic ring of the present disclosure is not limited to the examples described above.

A functional group containing at least one nitrogen, phosphorus, or sulfur may be, for example, any one selected from an amide group, an amine group, an imine group, an imide group, an azo group, a nitrile group, a phosphine group, a phosphoric acid group, a sulfonic group, a sulfonic acid group, and a thiocyanic group. However, the functional group containing at least one nitrogen, phosphorus, or sulfur is not limited to the examples described above.

The thiazole bond bonded to $A^1$ and $A^2$ forms n-conjugation to serve to stabilize the structure so that the covalent organic framework is not decomposed even during repeated charge and discharge.

An azo bond group (N=N) between $A^1$ and $A^2$ serves to transfer two electrons rapidly at a low potential by the following Reaction Formula 1:

[Reaction Formula 1]

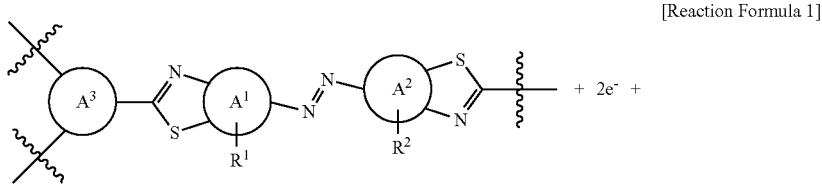

-continued

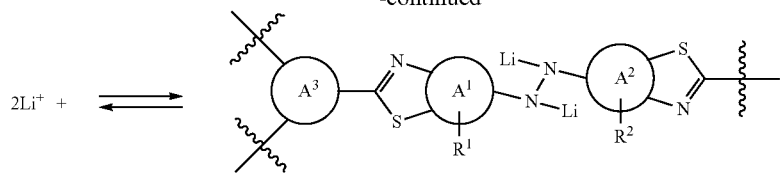

Since the N—N bond which is a single bond group forms different electrochemical reactions depending on a surrounding functional group or molecular structure and an electrolyte solution, it is difficult to expect the characteristics of the bond, and small molecules such as $AZO\text{-}NH_2$, AZO-COOH, and AZO-diCOOH are dissolved in an electrolyte solution or undergo an irreversible reaction to have bad cycle properties.

The covalent organic framework according to one embodiment is not decomposed in an electrolyte solution even during repeated charge and discharge due to a thiazole bond to secure structural stability, and transfers two electrons rapidly due to an azo bond to secure rapid charge and discharge characteristics.

The covalent organic framework according to another embodiment of may include a regular hexagonal structure having one side formed by the repeating unit of Chemical Formula 1 and being provided with a pore inside. In order to secure sufficient ion conductivity when the covalent organic framework is applied as an electrode material, lithium ions may easily pass through the pore in the covalent organic framework. From the above point of view, for securing excellent ion conductivity, the pore diameter may be 1.0 nm or more. From the above point of view, the pore diameter may be, for example, 1.5 nm or more, 2.0 nm or more, or 2.5 nm or more. However, when the pore diameter is excessively large, the chemical structure of the covalent organic framework becomes unstable and an energy density during charge and discharge may be low. Taking this into account, the pore diameter may be 8.0 nm or less. From the above point of view, the pore diameter may be, for example, 7.0 nm or less, 5.0 nm or less, or 3.5 nm or less.

The covalent organic framework according to one embodiment may include a structure represented by the following Chemical Formula 2:

[Chemical Formula 2]

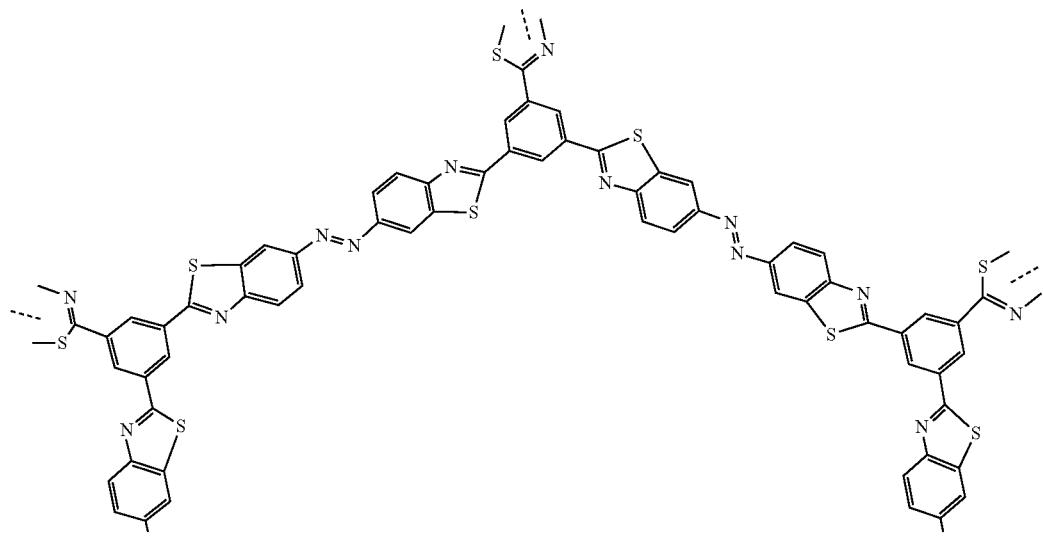

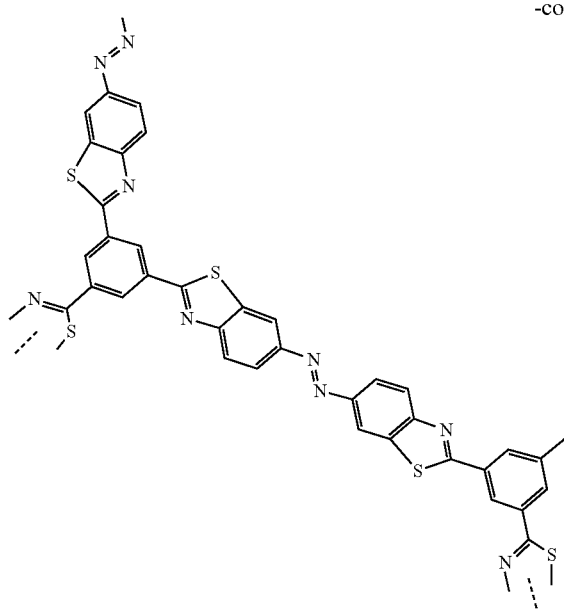
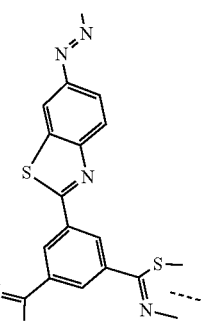

wherein the repeating unit is represented as follows:

[Repeating unit in Chemical Formula 2]

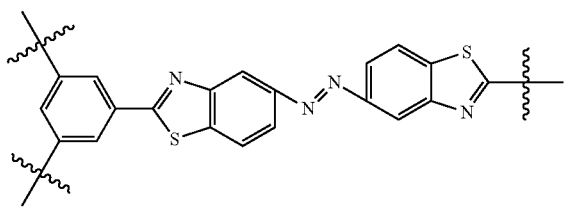

The covalent organic framework according to one embodiment may include a two-dimensional sheet in which the repeating unit of Chemical Formula 1 is horizontally arranged. For example, in the two-dimensional sheet, the repeating units of Chemical Formula 1 described above are horizontally arranged in a polygonal structure having a pore inside.

The polygon may be, for example, a regular or irregular triangle, quadrangle, pentagon, hexagon, or a combination thereof, and is not particularly limited as long as it has a pore inside. Considering sufficient ion conductivity and chemical structural stability, a polygon may be, for example, a regular triangle, quadrangle, pentagon, hexagon, or a combination thereof, or, for example, a regular pentagon, hexagon, or a combination thereof, or, for example, a regular hexagon. When the polygon is a regular hexagon, the two-dimensional sheet has a honeycomb structure to have properties of being light and strong against bending and compression.

The covalent organic framework according to one embodiment may include a three-dimensional mesoporous structure in which a plurality of the sheets are vertically arranged in any one stacking mode selected from a staggered stacking mode, an alternating stacking mode, a unidirectional stacking mode, a random stacking mode, and an eclipsed stacking mode.

The covalent organic framework according to one embodiment may include a three-dimensional mesoporous framework which is vertically arranged in an eclipsed stacking mode. According to embodiments of the present invention, the covalent organic framework is vertically arranged in an eclipsed stacking mode, so that it is strong and has excellent elasticity to be good for being applied to a light and flexible electrode. According to embodiments of the present invention, when the covalent organic framework is formed of a three-dimensional mesoporous framework, lithium ions may be easily transported to secure sufficient ion conductivity.

A spacing between the vertically arranged sheets may be, for example, 1.0 nm or less, 0.7 nm or less, or 0.5 nm or less.

The covalent organic framework according to embodiments of the present invention may be utilized in various technical fields, and for example, may be utilized as an electrode material of a battery. The battery may be various secondary batteries, and though it is not particularly limited, may be, for example, a lithium battery, a lithium-organic hybrid battery, and an alkaline battery.

The method of preparing a covalent organic framework according to one embodiment may include: reacting a first monomer including a diamine represented by the following Chemical Formula 3 and a second monomer represented by Chemical Formula 4 to obtain a covalent organic framework intermediate including a repeating represented by the following Chemical Formula 5 and reacting the covalent organic framework intermediate and sulfur to obtain the covalent organic framework according to Chemical Formula 1 described above:

[Chemical Formula 3]

[Chemical Formula 4]

[Chemical Formula 5]

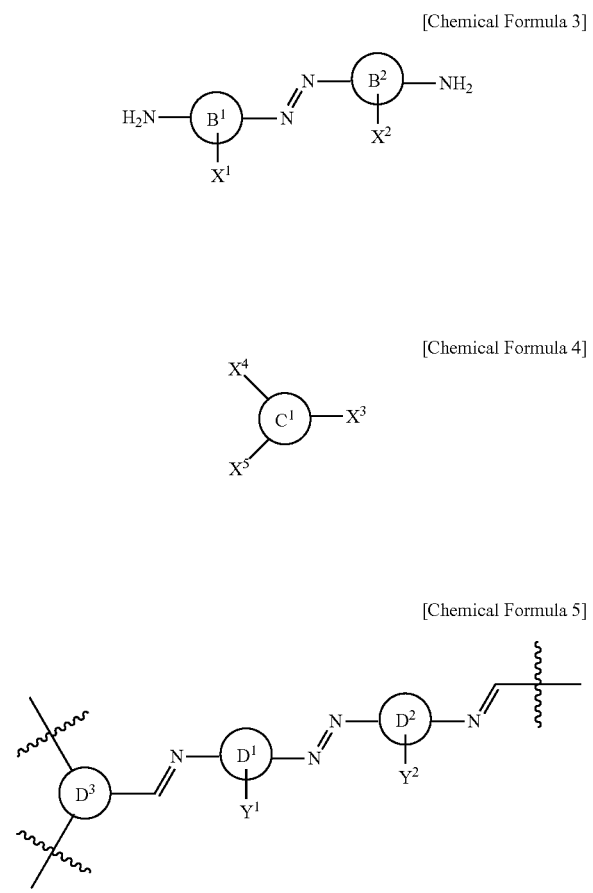

wherein in Chemical Formula 3, $B^1$ and $B^2$ are the same as or different from each other, and are independently of each other a monocyclic or polycyclic aromatic ring, and $X^1$ and $X^2$ are the same as or different from each other, and are independently of each other any one selected from hydrogen, a functional group containing at least one nitrogen, phosphorus, or sulfur, an unsubstituted or substituted C1-C6 alkyl group, an unsubstituted or substituted C2-C6 alkenyl group, an unsubstituted or substituted C2-C6 alkynyl group, and an unsubstituted or substituted C1-C6 alkoxy group, in Chemical Formula 4, $C^1$ is a monocyclic or polycyclic aromatic ring, and $X^3$, $X^4$, and $X^5$ are the same as or different from one another, and are independently of one another a functional group including at least one of an aldehyde group, a ketone group, a carboxyl group, an ester group, and an amide group, and in Chemical Formula 5, $D^1$, $D^2$, and $D^3$ are the same as or different from one another, and are independently of one another a monocyclic or polycyclic aromatic ring, and $Y^1$ and $Y^2$ are the same as or different from each other, and are independently of each other any one selected from hydrogen, a functional group containing at least one nitrogen, phosphorus, or sulfur, an unsubstituted or substituted C1-C6 alkyl group, an unsubstituted or substituted C2-C6 alkenyl group, an unsubstituted or substituted C2-C6 alkynyl group, and an unsubstituted or substituted C1-C6 alkoxy group.

In Chemical Formulae 3 to 5, the monocyclic aromatic ring may be, for example, unsubstituted or substituted benzene or aromatic heterocyclic compound. However, the monocyclic aromatic ring of the present disclosure is not limited to the examples described above.

In Chemical Formulae 3 to 5, the polycyclic aromatic ring may be, for example, an unsubstituted or substituted bicyclic aromatic ring such as naphthalene and azulene; a tricyclic aromatic ring such as anthracene, phenanthrene, and fluorene; a tetracyclic aromatic ring such as tetracene and pyrene; or a combination thereof, or a polycyclic aromatic ring derived therefrom, and may contain one or more heterocycles. However, the polycyclic aromatic ring of the present disclosure is not limited to the examples described above.

In Chemical Formula 3 and 5, a functional group containing at least one nitrogen, phosphorus, or sulfur may be, for example, any one selected from an amide group, an amine group, an imine group, an imide group, an azo group, a nitrile group, a phosphine group, a phosphoric acid group, a sulfonic group, a sulfonic acid group, and a thiocyanic group. However, the functional group containing at least one nitrogen, phosphorus, or sulfur is not limited to the examples described above.

According to one embodiment, the diamine of Chemical Formula 3 may be 4,4'-azodianiline.

According to another embodiment, Chemical Formula 4 may be 1,3,5-triformylbenzene.

An amine group (—$NH_2$) at both ends of the diamine of Chemical Formula 3 reacts with any one of an aldehyde group, a ketone group, a carboxyl group, an ester group, and an amide group of Chemical Formula 4 to form an imide bond (C=NH) of the repeating unit of Chemical Formula 5. Considering the reaction of the diamine of Chemical Formula 3 and Chemical Formula 4, a stoichiometric reaction molar ratio between the first monomer and the second monomer may be, for example, 1:0.5 to 1:1.5.

In the repeating unit of Chemical Formula 5, an imide bond (C=NH) is formed by a reaction of an amine group (—$NH_2$) at both ends of the diamine of Chemical Formula 3 and any one of an aldehyde group, a ketone group, a carboxyl group, an ester group, and an amide group, $D^3$ is derived from $C^1$, and D1 and $D^2$ are derived from B1 and B2, respectively.

For better understanding, the covalent organic framework intermediate including the repeating unit of Chemical Formula 5, for example, may include a structure represented by the following Chemical Formula 6:

[Chemical Formula 6]

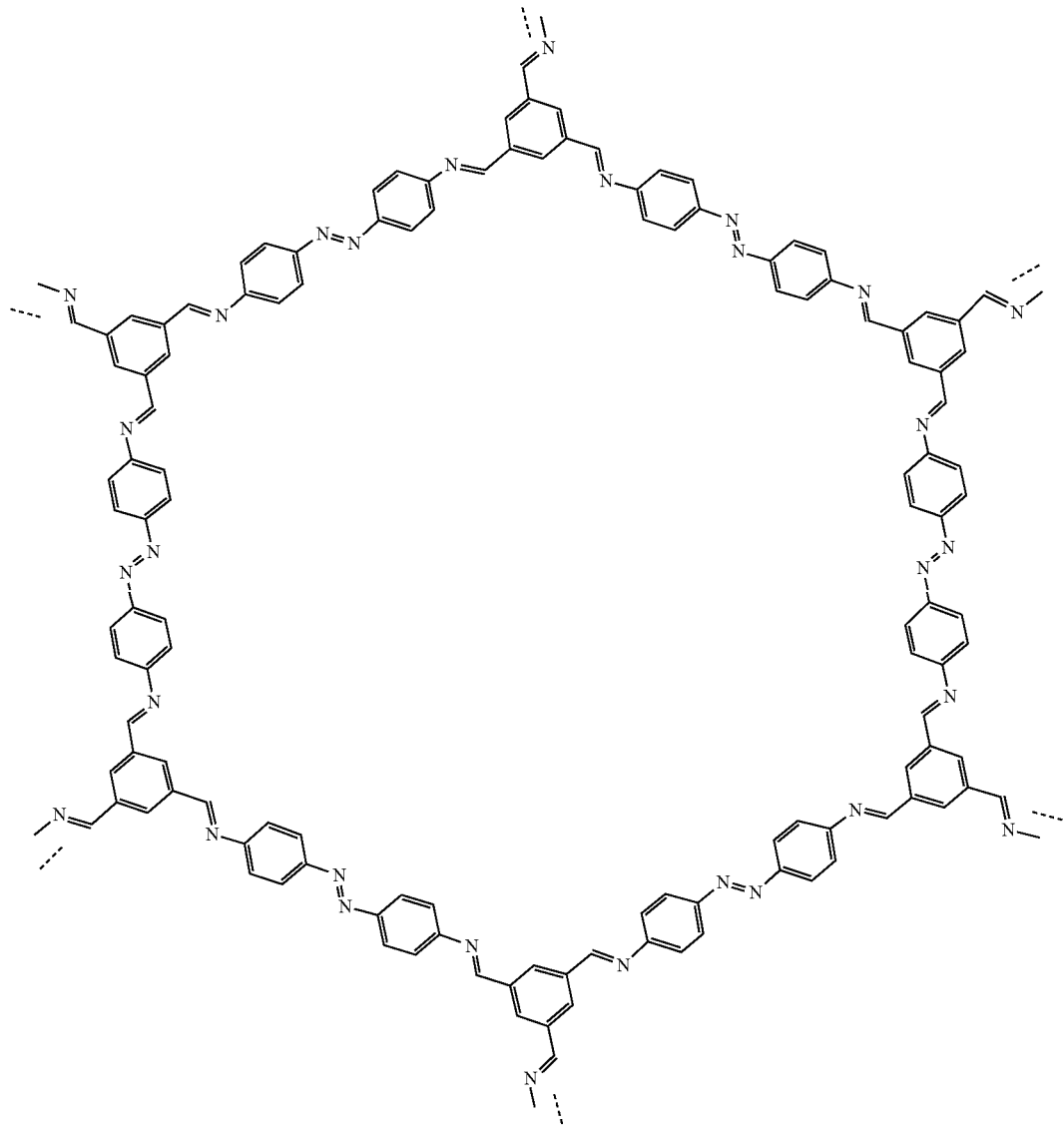

wherein the repeating unit is represented as follows:

[Repeating unit in Chemical Formula 6]

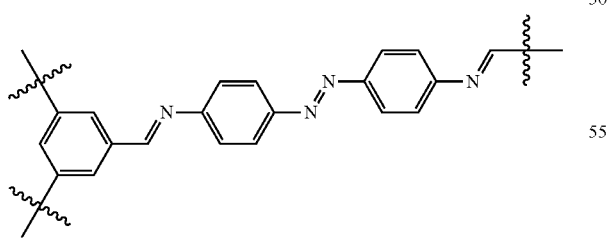

According to one embodiment, a reaction of the covalent organic framework intermediate including the repeating unit of Chemical Formula 5 with sulfur to obtain the covalent organic framework including the repeating unit of Chemical Formula 1 may include reacting an imine bond (C=NH) and sulfur to form a thiazole bonding ring as shown in the following Reaction Formula 2:

[Reaction Formula 2]

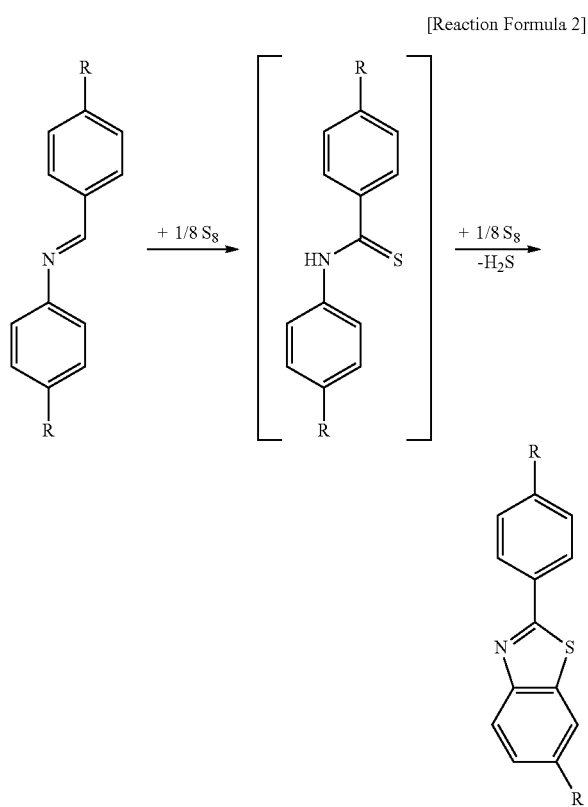

The step of reacting the covalent organic framework intermediate and sulfur according to one embodiment may include: providing the covalent organic framework intermediate and sulfur to a closed space in a vacuum, performing heating from 25° C. to 155° C. at a heating rate of 30 to 50° C./hr and at 155° C. for 3 hours, performing heating from 155° C. to 350° C. at a heating rate of 50 to 70° C./hr and then at 350° C. for 3 hours, and performing cooling to 25° C., Soxhlet extraction, and drying for 10 hours or more.

The Soxhlet extraction may include, for example, using toluene to perform Soxhlet extraction for 24 hours and then using tetrahydrofuran to perform Soxhlet extraction for 24 hours.

The method of preparing a covalent organic framework according to one embodiment may have a high yield, and the yield may be, for example, 50% or more, for example, 70% or more, and for example, 75% or more.

Examples

Hereinafter, the examples of the present invention will be described in detail with reference to the attached drawings. However, it is provided so that the present invention may be easily carried out by those skilled in the art, the present invention may be implemented in various forms, and the idea of the present invention is not necessarily limited to the examples.

Example 1: Preparation of Covalent Organic Framework (AZO-1)

150 mg (0.925 mmol) of 1,3,5-triformylbenzene (TB) and 295 mg (1.39 mmol) of 4,4'-azodianiline (AZO-$NH_2$) were introduced to a three-neck round bottom flask, and then side necks were sealed by a rubber diaphragm. The sealed flask was vented with argon and with vacuum three times repeatedly. 2 ml of anhydrous 1,4-dioxane and 2 ml of anhydrous mesitylene were injected into the sealed flask with a syringe, and then ultrasonication was performed. Thereafter, 0.1 ml of 6 M acetic acid was added to the flask, and the flask was heated to 120° C. for 5 days under an argon atmosphere without stirring. Produced precipitates were filtered, cooled to room temperature, and washed with anhydrous DMF, ethanol, and acetone in that order. Thereafter, anhydrous tetrahydrofuran was used to perform Soxhlet extraction for 24 hours, and drying at 120° C. for 16 hours was performed in a Buchi vacuum oven to obtain a covalent organic framework intermediate, AZO-2.

100 mg of the prepared covalent organic framework intermediate, AZO-2 was pulverized with sulfur at 10 times the mass at room temperature using a mortar and pestle. A uniform mixture of AZO-2/sulfur was transferred to a Pyrex tube, and the tube was vented with argon and with vacuum three times repeatedly. The tube was sealed in a vacuum state, heated from room temperature (25° C.) to 155° C. at a heating rate of 43.33° C./hr, and then heated at 155° C. for 3 hours. Thereafter, the tube was heated from 155° C. to 350° C. at a heating rate of 65° C./hr, heated at 350° C. for 3 hours, and then cooled down to 25° C. The powder obtained by cooling was subjected to Soxhlet extraction for 24 hours using toluene, and then subjected to Soxhlet extraction for 24 hours using tetrahydrofuran, and then was washed using toluene. Thereafter, drying at 160° C. for 16 hours was performed in a Buchi vacuum oven to obtain a covalent organic framework AZO-1. Here, the yield of the covalent organic framework AZO-1 was about 75%.

Comparative Example 1: Preparation of Covalent Organic Framework (AZO-2)

AZO-2 was obtained in the same manner as the method of obtaining the covalent organic framework intermediate AZO-2 of Example 1.

Comparative Example 2: Preparation of Covalent Organic Framework (AZO-3)

150 mg (0.714 mmol) of 1,3,5-triformylphloroglucinol (TP) and 227 mg (1.06 mmol) of 4,4'-azodianiline (AZO-$NH_2$) were mixed in a glass vial, 5 ml of anhydrous 1,4-dioxane was added thereto, and ultrasonication was performed for 30 seconds. Thereafter, 1.8 ml of deionized water and 1.2 ml of glacial acetic acid were sequentially injected, and then the closed vial was heated to 80° C. for 5 days. Produced precipitates were filtered, cooled to room temperature, and washed with anhydrous DMF, ethanol, and acetone in that order. Thereafter, anhydrous tetrahydrofuran was used to perform Soxhlet extraction for 24 hours, and drying at 120° C. for 16 hours was performed in a Buchi vacuum oven to obtain a covalent organic framework, AZO-3.

FIG. 1 attached is a drawing showing a preparation process of AZO-1 of Example 1, AZO-2 of Comparative Example 1, and AZO-3 of Comparative Example 2, and a pore diameter and an interlayer spacing of the prepared covalent organic framework.

<Analysis of Structural Characteristics of Prepared Covalent Organic Framework>

Figure 2A:
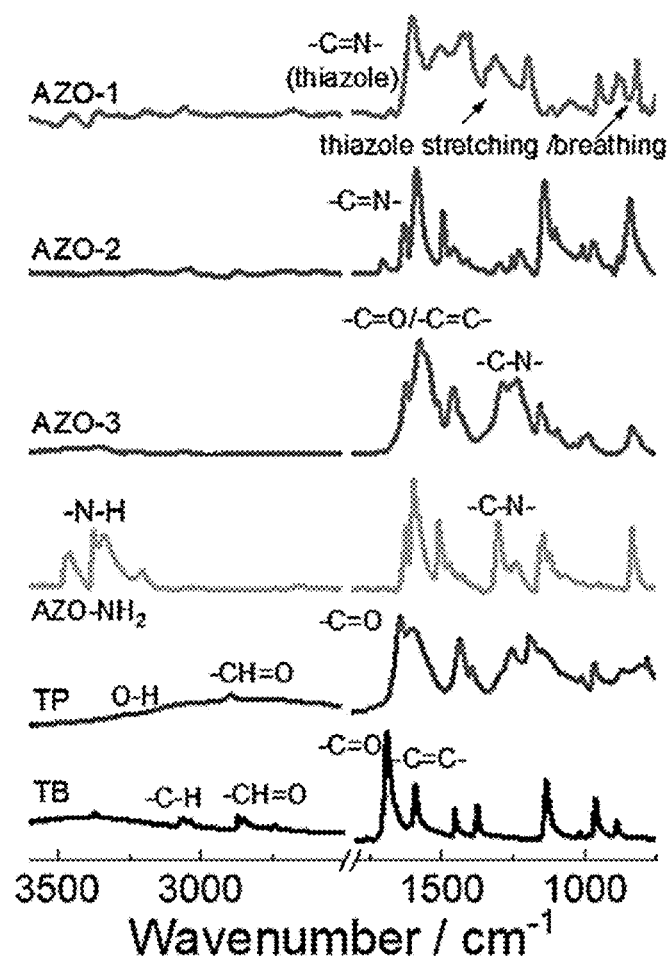
FIG. 2A is a graph of the results of analyzing attenuated total reflection-infrared (ATR-IR) spectra of Example 1 (AZO-1), Comparative Example 1 (AZO-2), and Comparative Example 2 (AZO-3).

FIG. 2A attached is a graph of the results of analyzing attenuated total reflection-infrared (ATR-IR) spectra of Example 1 (AZO-1), Comparative Example 1 (AZO-2), and Comparative Example 2 (AZO-3).

Figure 2B:
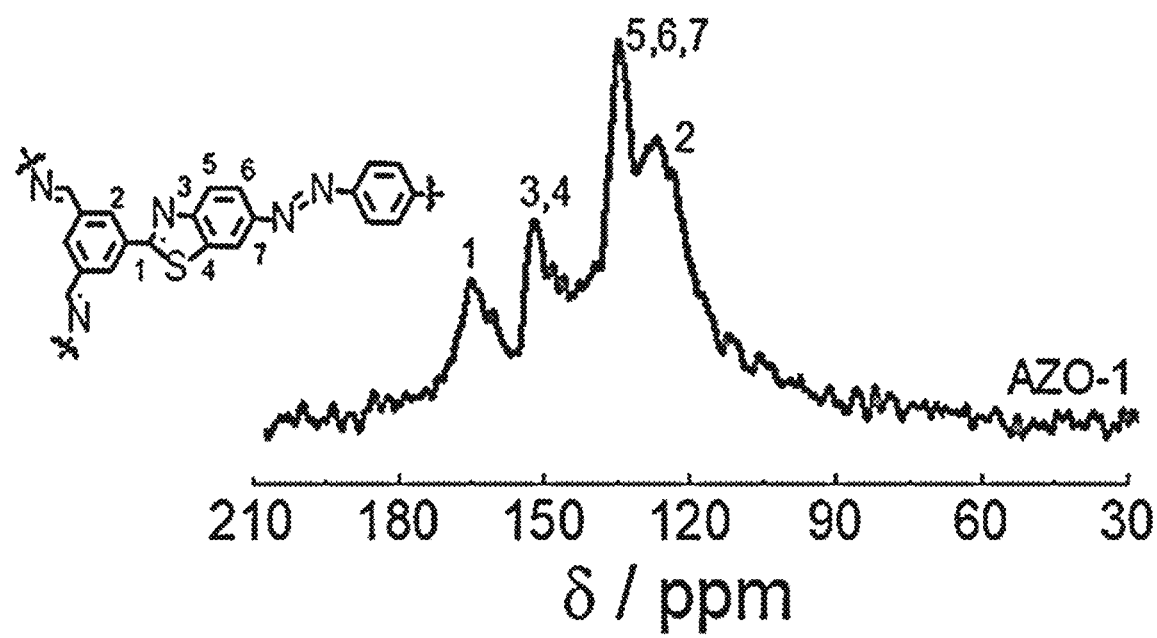
FIG. 2B is a graph of results of analyzing $^{13}C$ cross-polarization magic angle spinning solid state NMR spectra ($^{13}C$ CP/MAS NMR) of Example 1 (AZO-1), Comparative Example 1 (AZO-2), and Comparative Example 2 (AZO-3).

FIG. 2B attached is a graph of results of analyzing $^{13}C$ cross-polarization magic angle spinning solid state NMR spectra ($^{13}C$ CP/MAS NMR) of Example 1 (AZO-1), Comparative Example 1 (AZO-2), and Comparative Example 2 (AZO-3).

Figure 2C:
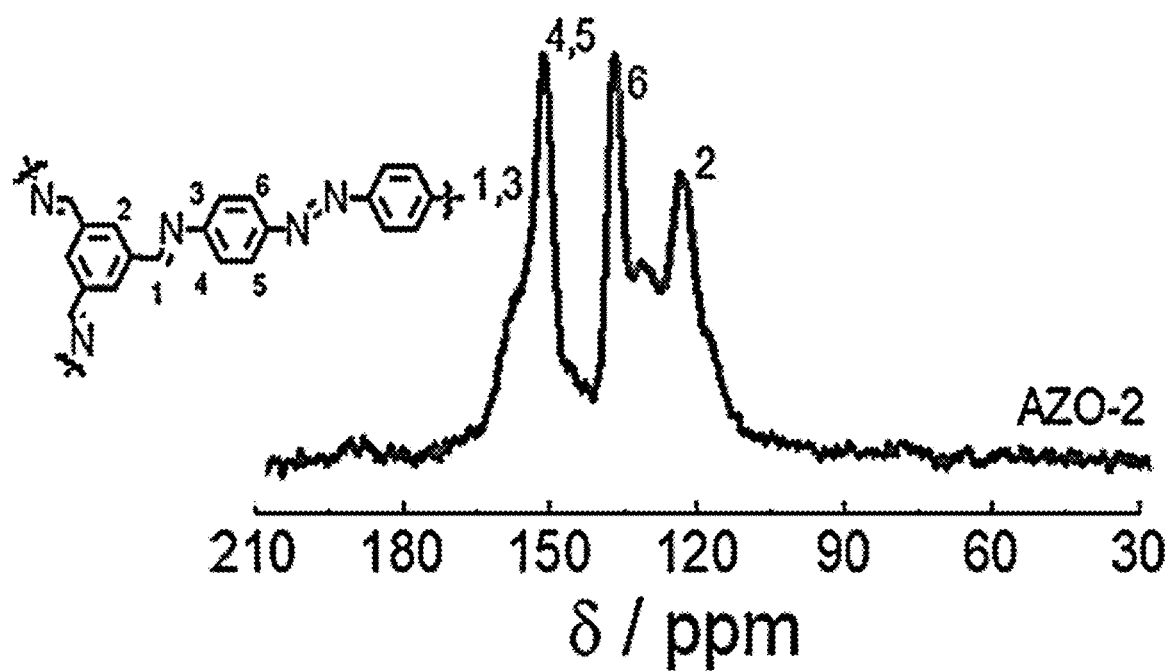
FIG. 2C is a graph of results of analyzing the Rietveld refinement and simulation of powder XRD of Example 1 (AZO-1), Comparative Example 1 (AZO-2), and Comparative Example 2 (AZO-3).
Figure 2D:
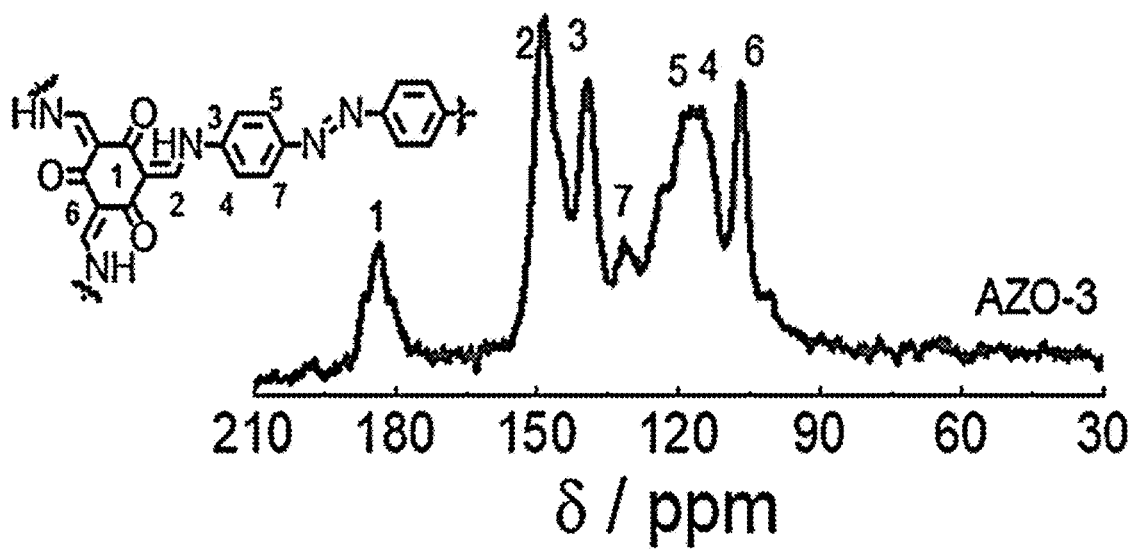
Figure 2E:
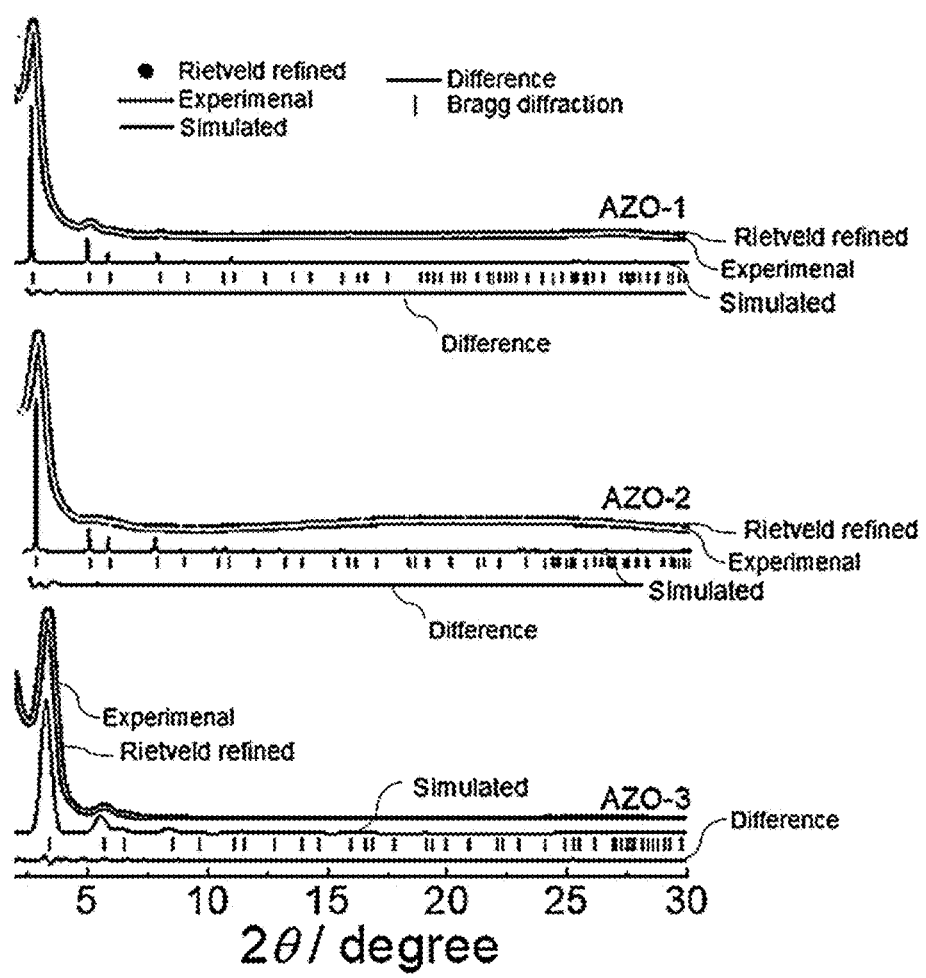

FIG. 2C attached is a graph of results of analyzing the Rietveld refinement and simulation of powder XRD of Example 1 (AZO-1), Comparative Example 1 (AZO-2), and Comparative Example 2 (AZO-3).

Referring to FIG. 2A, in Example 1 (AZO-1), Comparative Example 1 (AZO-2), and Comparative Example 2 (AZO-3), the N—H stretching band at 3300 $cm^{-1}$ of AZO-$NH_2$ disappeared by a covalent bond with a linkage molecule.

Referring to FIG. 2A, in Example 1 (AZO-1), breathing and stretching modes of a thiazole bond were shown at 945 $cm^{-1}$ and 1308 $cm^{-1}$, respectively, and referring to FIG. 2B, in Example 1 (AZO-1), C—S resonance was shown at 167 ppm and a little imine signal was shown at 153 ppm.

Referring to FIG. 2A, in Comparative Example 1 (AZO-2), a stretching band of imine was shown at 1620 $cm^1$, and this result corresponds to the $^{13}C$ NMR peak of FIG. 2B.

Referring to FIG. 2A, a keto-enol tautomer of Comparative Example 2 (AZO-3) was shown in a C—N stretching band at 120 $cm^1$ and overlapping C=O and C=C vibrations at 1580 $cm^1$.

Referring to FIG. 2C, Example 1 and Comparative Examples 1 and 2 all had a hexagonal P6/m space group structurally, and has an eclipsed stacking mode. Examples 1 and Comparative Examples 1 and 2 showed high 100 reflection at 2θ=~3.2°, and little 110, 200, 210, 001 reflections at 2θ=5.5°, 6.4°, 8.4°, and 27°, respectively. A unit cell parameter in Rietveld refinement showed similar in-plane lattice parameters (a and b) and similar stacking distances (c=3.3 to 3.5 Å) for Example 1 and Comparative Examples 1 and 2. Interlayer interaction including a thiazole bond was as strong as including imine. In particular, Example 1 (AZO-1) showed a narrower and sharper 0001 reflection as compared with Comparative Example 1 (AZO-2) to show that crystallinity was better. The characteristics of Example 1 (AZO-1) are distinguished from the results of the previous topochemical-conversion in which the covalent organic framework (COF) based on a triphenyl triazine thiazole bond showed a weaker interaction than imine.

In order to evaluate the electrochemical properties when an electrode was formed of the covalent organic framework, electrodes were manufactured by the covalent organic frameworks of Example 1 and Comparative Examples 1 and 2.

Example 2: Electrode Using Covalent Organic Framework (AZO-1)

The covalent organic framework (AZO-1) of Example 1, Super P carbon black, a polyvinylidene fluoride (PVDF) binder were dispersed in N-methyl-2-pyrrolidone at a weight ratio of 7:2:1. Thereafter, the dispersion was pulverized using mortar and pestle, and then homogenized to obtain a viscous slurry. The obtained slurry was cast on a Cu foil and dried at 80° C. for 24 hours using a heat oven for removing NMP to be manufactured into an electrode.

Comparative Example 3: Electrode Using Covalent Organic Framework (AZO-2)

An electrode was manufactured under the same conditions as in Example 2, except that the covalent organic framework (AZO-2) of Comparative Example 1 was used.

Comparative Example 4: Electrode Using Covalent Organic Framework (AZO-3)

An electrode was manufactured under the same conditions as in Example 2, except that the covalent organic framework (AZO-3) of Comparative Example 2 was used.

The manufactured electrode was used as a positive electrode, and a negative electrode obtained by attaching a lithium metal foil on a stainless steel substrate, a glass microfiber (GF/C) membrane as a separator and an electrolyte solution in which 1.0 M LiFSI as a lithium salt was mixed with an organic solvent (DOL:DME:1:1 vol %) were used to manufacture a CR2032 type coin cell. The manufacturing process of the coin cell was performed in a glove box filled with Ar ($H_2O$ and $O_2$<0.5 ppm).

<Evaluation of Electrochemical Properties of Prepared Covalent Organic Framework>

1. Cyclic Voltammetry (CV)

A biologic VMP3 tester was used to perform cyclic voltammetry (CV) for Example 2, and Comparative Examples 3 and 4. All potentials measured were indicated as Li/Li$^+$, unless otherwise particularly stated. CV was recorded as being in a range of 1.0 to 3.0 V at an increased scan speed of 0.1 to 0.5 $mVs^{-1}$.

Figure 3A:
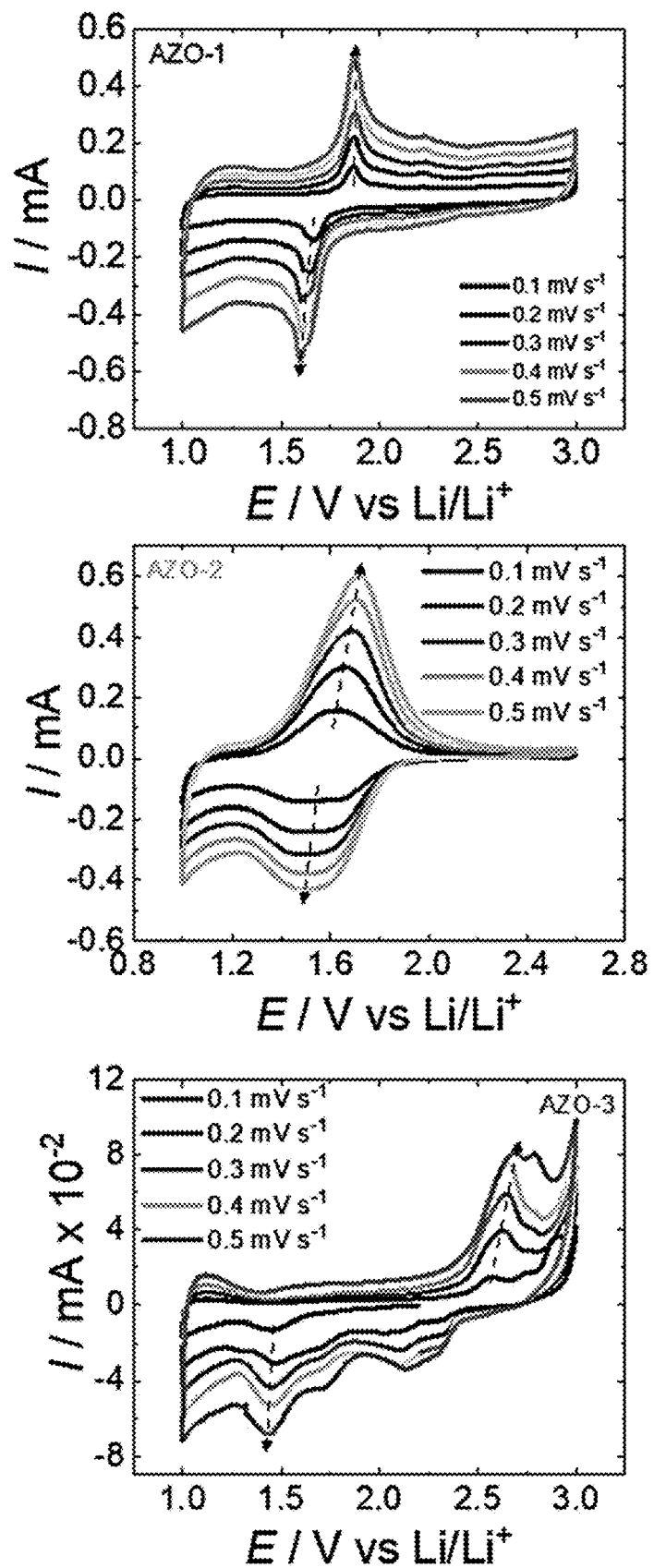
FIG. 3A is a cyclic voltammetric diagram (CV) at a scan speed of 0.1 to 0.5 mV·s$^{-1}$.
Figure 3B:
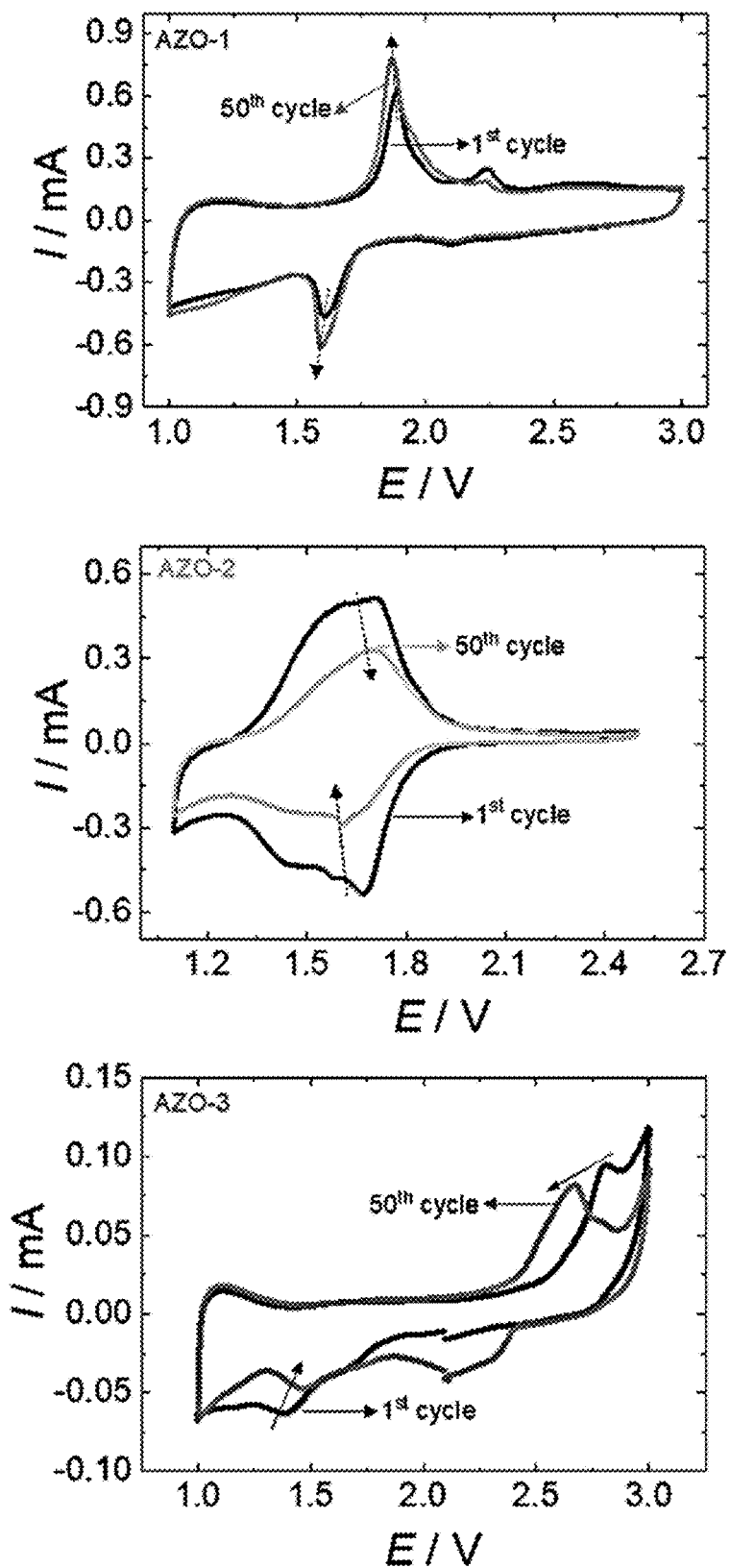
FIG. 3B is a cyclic voltammetric diagram (CV) at 1 to 50 cycles.

FIG. 3A attached is a cyclic voltammetric diagram (CV) at a scan speed of 0.1 to 0.5 $mV·s^{-1}$. FIG. 3B is a cyclic voltammetric diagram (CV) at 1 to 50 cycles. Referring to FIGS. 3A and 3B, Example 2 (AZO-1) showed a single and irreversible azo redox reaction at 1.5 to 2.0 V. In particular, the single azo redox signal of Example 2 (AZO-1) was not split even at a very slow scan speed and during repeated cycling, and it was shown that rapid two-electron transfer was possible both at an oxidation reaction and a reduction reaction. In addition, in Example 2 (AZO-1), the electrode was wet by cycling, so that a redox signal was increased. Referring to FIG. 3B, it was found that in Example 2 (AZO-1), two Li$^+$ ions were bonded at the same time to an azo group in a pair at about 1.65 V.

In contrast, referring to FIG. 3B, Comparative Example 3 (AZO-2) showed two sets of gentle redox peaks at 1.4 to 1.7 V assigned to two-electron transfer of an azo reactor. This result shows that an azo group integrated with an imine bond has slower two-electron transfer. In particular, in Comparative Example 3 (AZO-2), current was greatly decreased after 50 cycles due to the low chemical stability of imine.

In Comparative Example 4 (AZO-3), no signal of redox reaction was shown after a reduction reaction occurred at 1.4 to 2.0 V. This shows that the azo redox reaction occurred irreversibly in the presence of a β-ketoenamine bond. Instead of this, a new waveform occurred at 2.0 to 3.0 V by a redox reaction of a carbonyl group (C=0/C–0).

2. Galvanostatic Examination

Galvanostatic examination was performed at room temperature using a PNE battery cycler (model PESC05-0.1). A galvanostatic cycle was set in a range of 1.2 to 2.6 V in Example 2 and Comparative Example 3, and in a range of 1.0 to 3.0 V in Comparative Example 4. Before the galvanostatic examination, a pre-activation process of performing 50 cycles at 0.5 mV·s$^{-1}$ was performed.

Figure 4A:
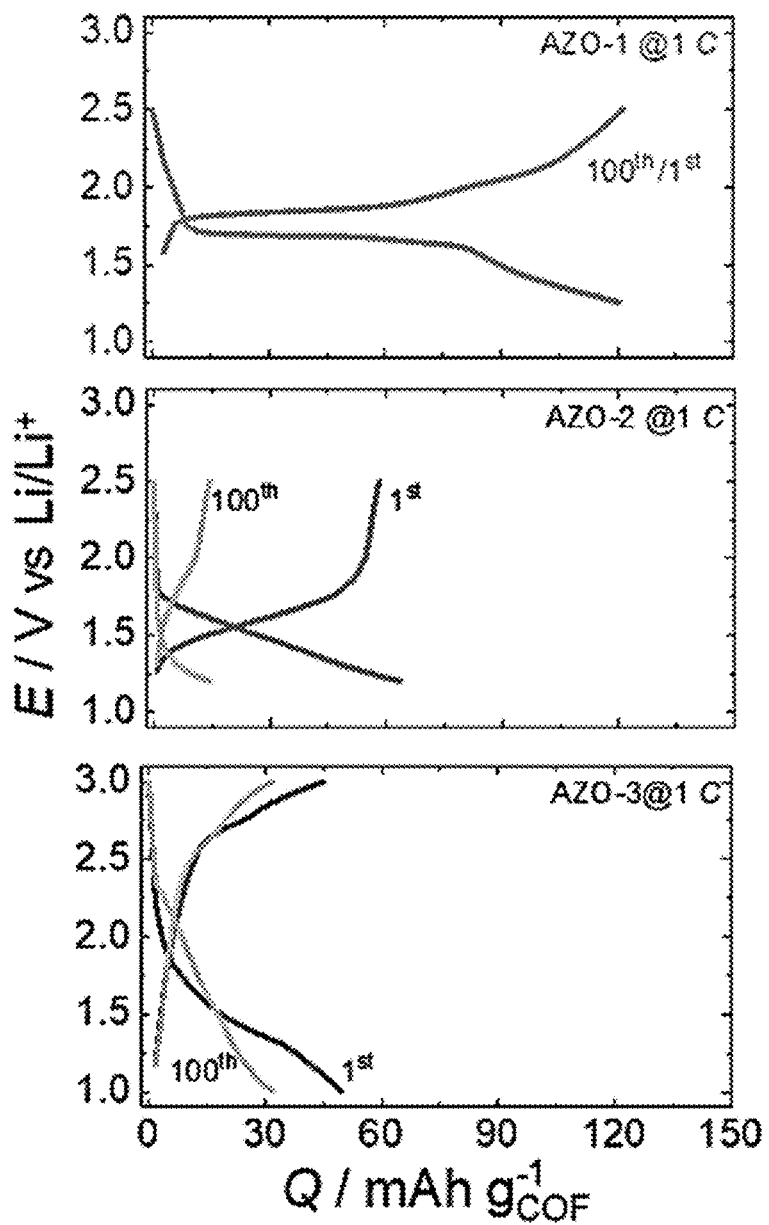
FIG. 4A is a constant current profile at the 1st cycle and the 100th cycle of Example 2 (AZO-1), Comparative Example 3 (AZO-2), and Comparative Example 4 (AZO-3) in a potential range of 1.2 to 2.6 V.
Figure 4B:
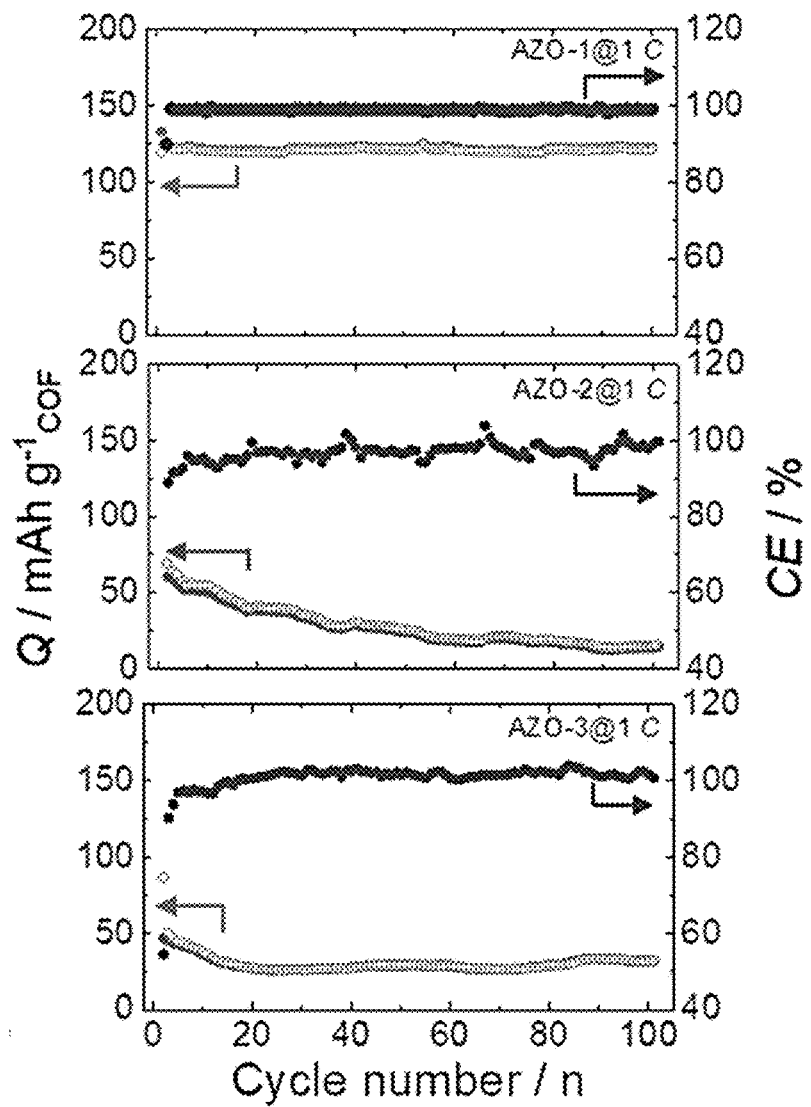
FIG. 4B is a drawing representing a capacity (Q) and a coulombic efficiency (CE) depending on the number of cycles of Example 2 (AZO-1), Comparative Example 3 (AZO-2), and Comparative Example 4 (AZO-3).
Figure 4C:
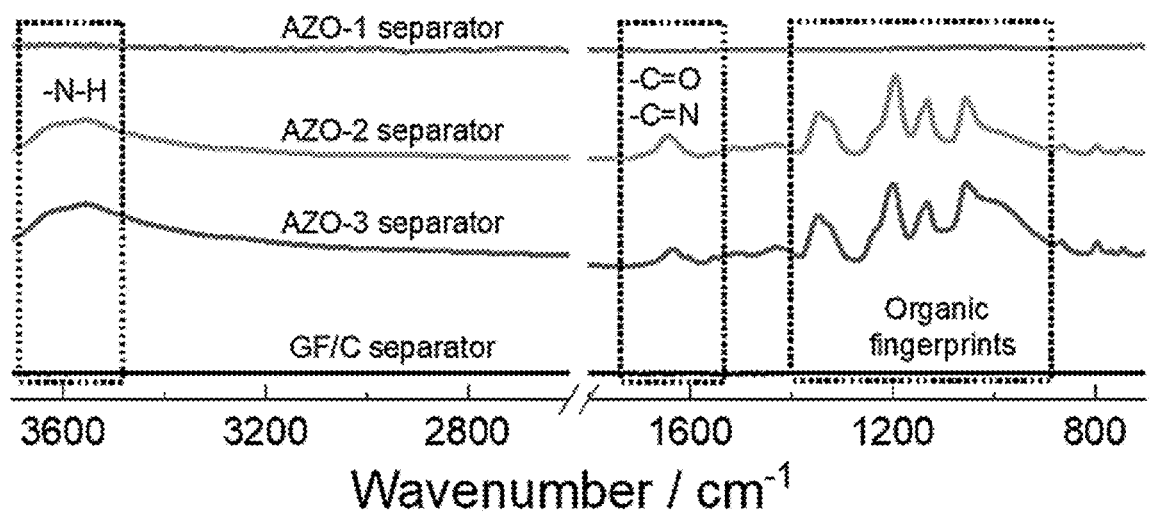
FIG. 4C shows results of analyzing ATR-IR spectra of a separator surface forming a battery after the 100th cycle of Example 2 (AZO-1), Comparative Example 3 (AZO-2), and Comparative Example 4 (AZO-3).
Figure 5A:
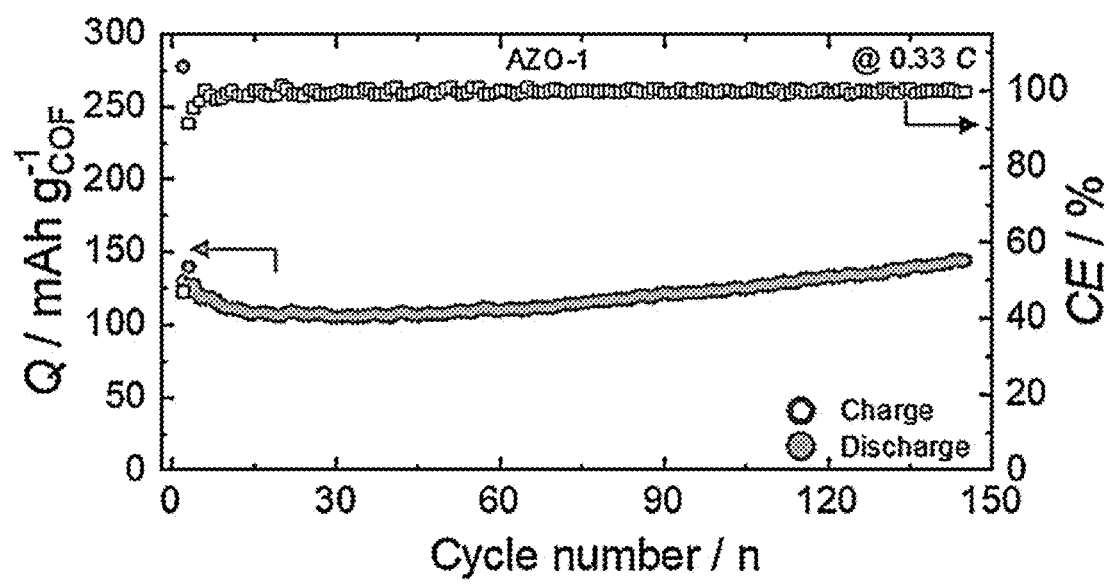
FIGS. 5A to 5D are graphs illustrating a capacity depending on the charge and discharge cycles of Example 2 (AZO-1).
Figure 5B:
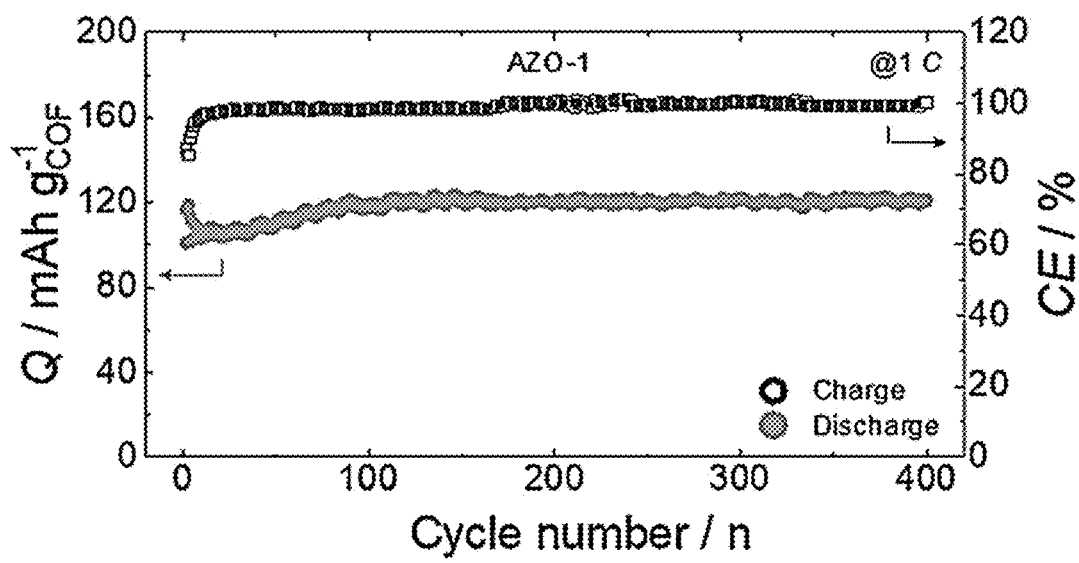
Figure 5C:
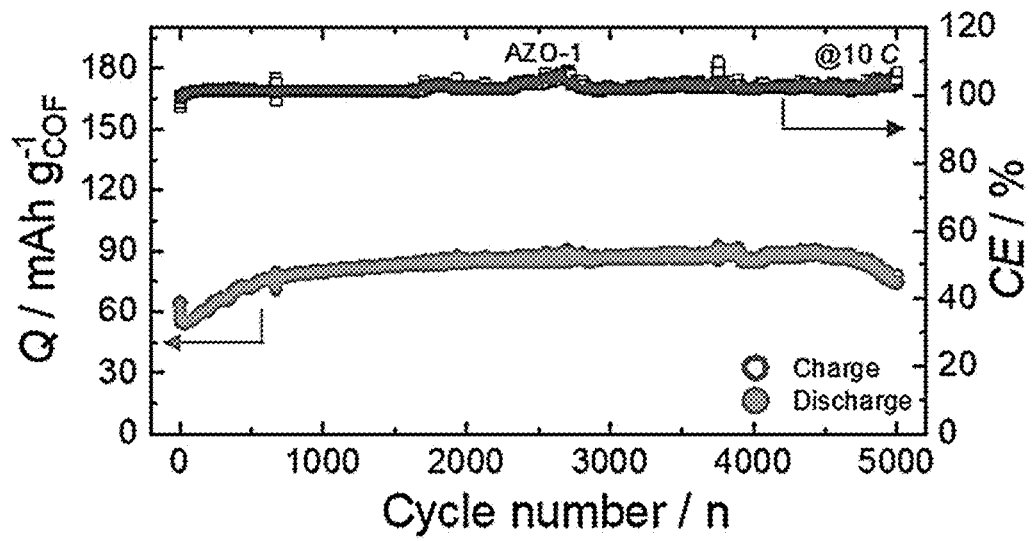
Figure 5D:
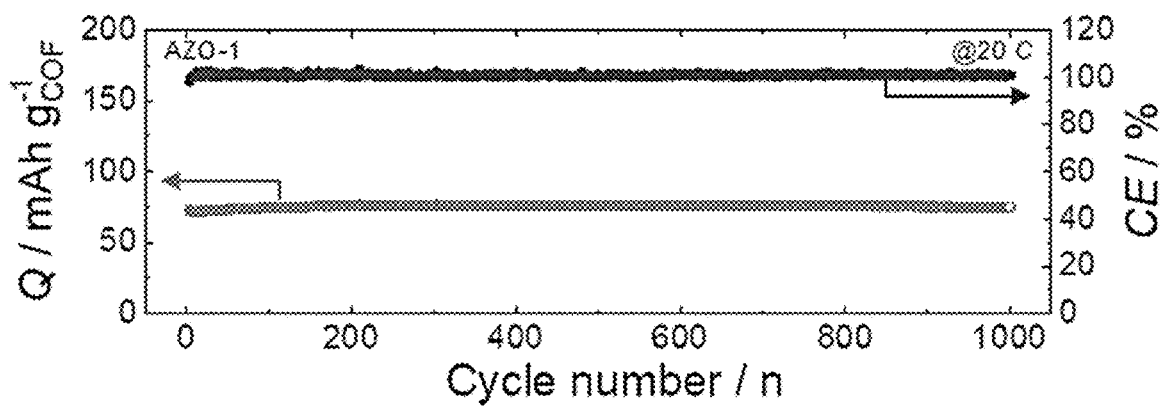

FIG. 4A attached is a galvanostatic profile at the 1st cycle and the 100th cycle of Example 2 (AZO-1), Comparative Example 3 (AZO-2), and Comparative Example 4 (AZO-3) in a potential range of 1.2 to 2.6 V. FIG. 4B attached is a drawing representing a capacity (Q) and a coulombic efficiency (CE) depending on the number of cycles of Example 2 (AZO-1), Comparative Example 3 (AZO-2), and Comparative Example 4 (AZO-3). In FIGS. 4A and 4B, discharge was performed under the condition of 1C to 1.2 V. FIG. 4C attached shows results of analyzing ATR-IR spectra of a separator surface forming a battery after the 100th cycle of Example 2 (AZO-1), Comparative Example 3 (AZO-2), and Comparative Example 4 (AZO-3). Using a separator (GF/C) spectrum as a base line, when a spectrum signal is changed, it may be interpreted that the electrode is decomposed so that there is an organic residue on the separator.

Referring to FIG. 4A, Example 2 (AZO-1) had a capacity of about 120 mAh·g$^{-1}$ at the time of discharge to 1.2 V, and this value showed a high capacity with a little lower value as compared with 145 mAh·g$^{-1}$ which is a theoretical capacity based on a two-electron transfer event. A constant potential plateau was shown at about 1.65 V during discharge and a polarization of only 130 mV was shown. In addition, referring to FIG. 4B, Example 2 (AZO-1) showed a coulombic efficiency of 99.9% to 100 cycles and a capacity retention rate of 99.999%. Referring to FIG. 4C, almost no organic residue remains on the separator, and thus, it was found that the electrode was not decomposed and was structurally stable. From the results of FIGS. 4A to 4C, it was found that Example 2 (AZO-1) had a high capacity and was structurally very stable even in repeated cycles.

However, referring to FIG. 4B, in Comparative Example 3 (AZO-2), the capacity after 100 cycles was rapidly decreased to 29% relative to the initial capacity. This resulted from the structural decomposition of the covalent organic framework caused by the chemical instability of an imine bond. Referring to FIG. 4C, on the separator of Comparative Example 3 (AZO-2), an organic residue such as monomer and oligomer fragments was detected. In addition, Comparative Example 3 (AZO-2) was easily decomposed and dissolved in an electrolyte solution even without an electrochemical reaction.

Referring to FIG. 4A, Comparative Example 4 (AZO-3) showed a very large polarization curve. Referring to FIG. 4C, Comparative Example 4 (AZO-3) had a capacity of about 40 mAh·g$^{-1}$ after 100 cycles. Considering that the capacity of a carbonyl group is about 30 mAh·g$^{-1}$ and the capacity of Super P carbon black is about 5 mAh·g$^{-1}$, the contribution of an azo redox reaction to a capacity in Comparative Example 4 (AZO-3) may be neglected. In Comparative Example 4 (AZO-3), the covalent organic framework was decomposed due to the non-conjugated structure of β-ketoeneamine, and referring to FIG. 4C, on the separator of Comparative Example 4 (AZO-3), an organic residue due to the decomposition of the covalent organic framework was detected.

3. Rate Capability Evaluation

The rate capability of Example 2 (AZO-1) was tested. A stable capacity maintenance of Example 2 (AZO-2) from 0.5 C to 20 C was evaluated. Here, the number of cycles was set as 145 at 0.33 C, 400 at 1 C, 4500 at 10 C, and 1000 at 20 C. FIGS. 5A to 5D attached are graphs illustrating the capacity depending on charge and discharge cycles, and in FIGS. 5A to 5D, the C-rate and the number of cycles were 145 at 0.33 C, 400 at 1 C, and 1000 at 20 C, respectively.

Referring to FIGS. 5A to 5D, in Example 2 (AZO-1), the coulombic efficiency was 99.999% or more and a stable capacity was maintained.

4. Impedance Analysis

Figure 6A:
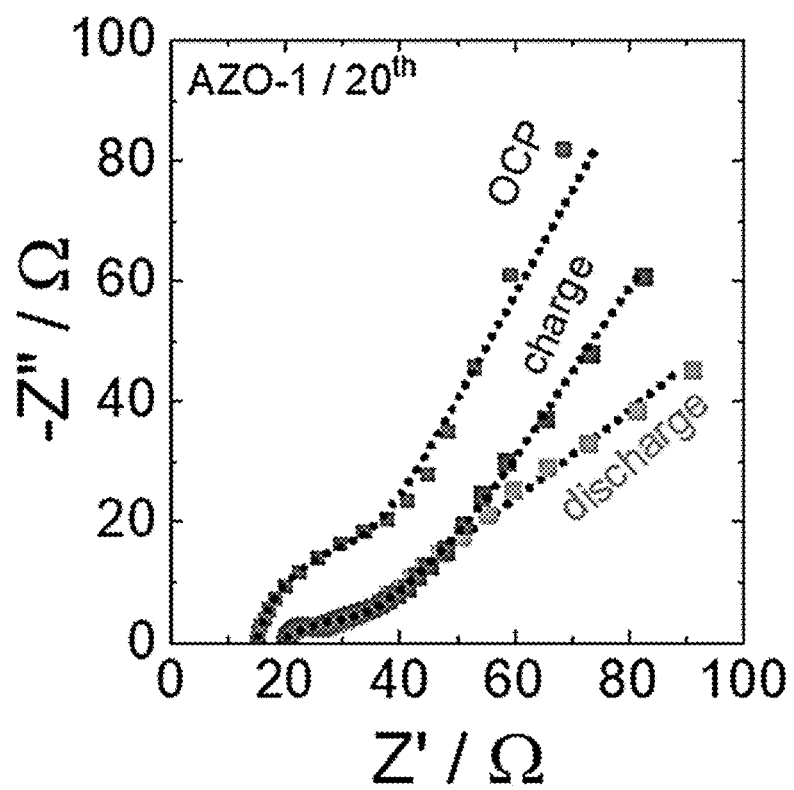
FIGS. 6A to 6C are Nyquist plots of Example 2 (AZO-1), Comparative Example 3 (AZO-2), and Comparative Example 4 (AZO-3) after performing 20 charge and discharge cycles at an open circuit potential (OCP), respectively.
Figure 6B:
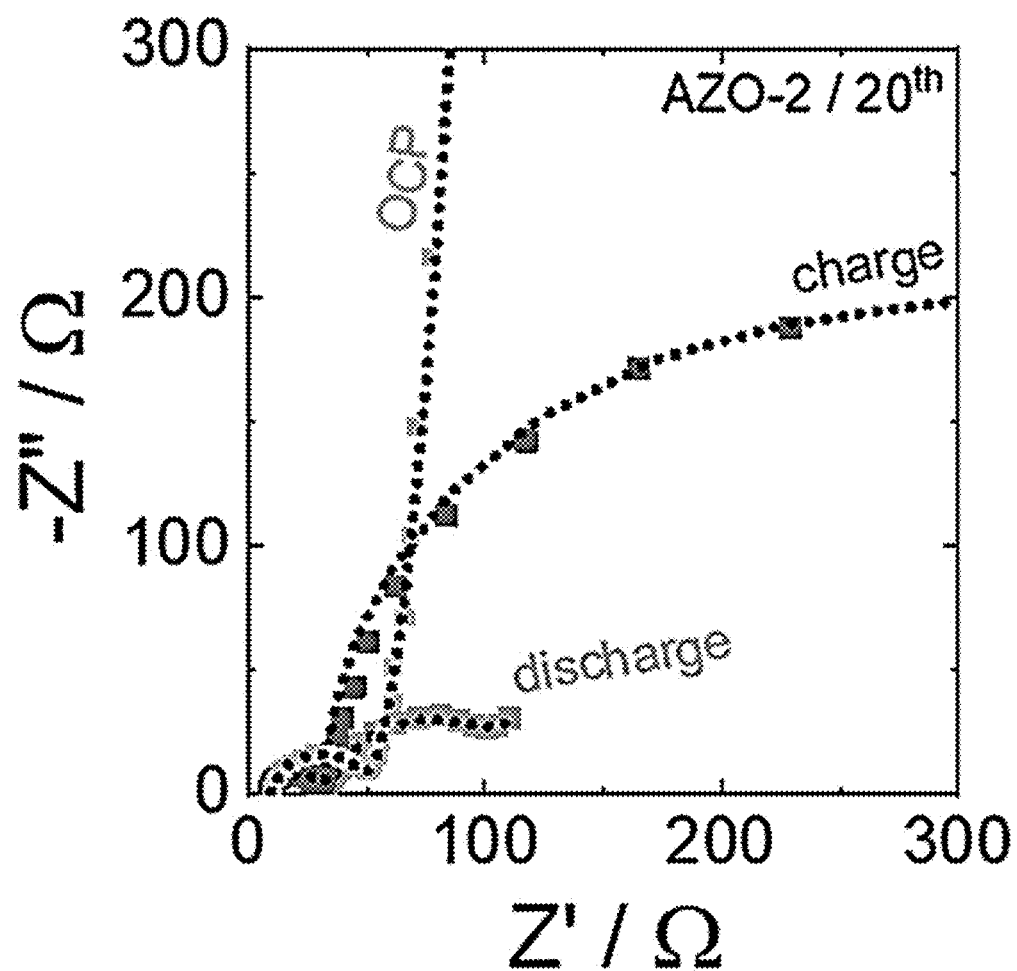
Figure 6C:
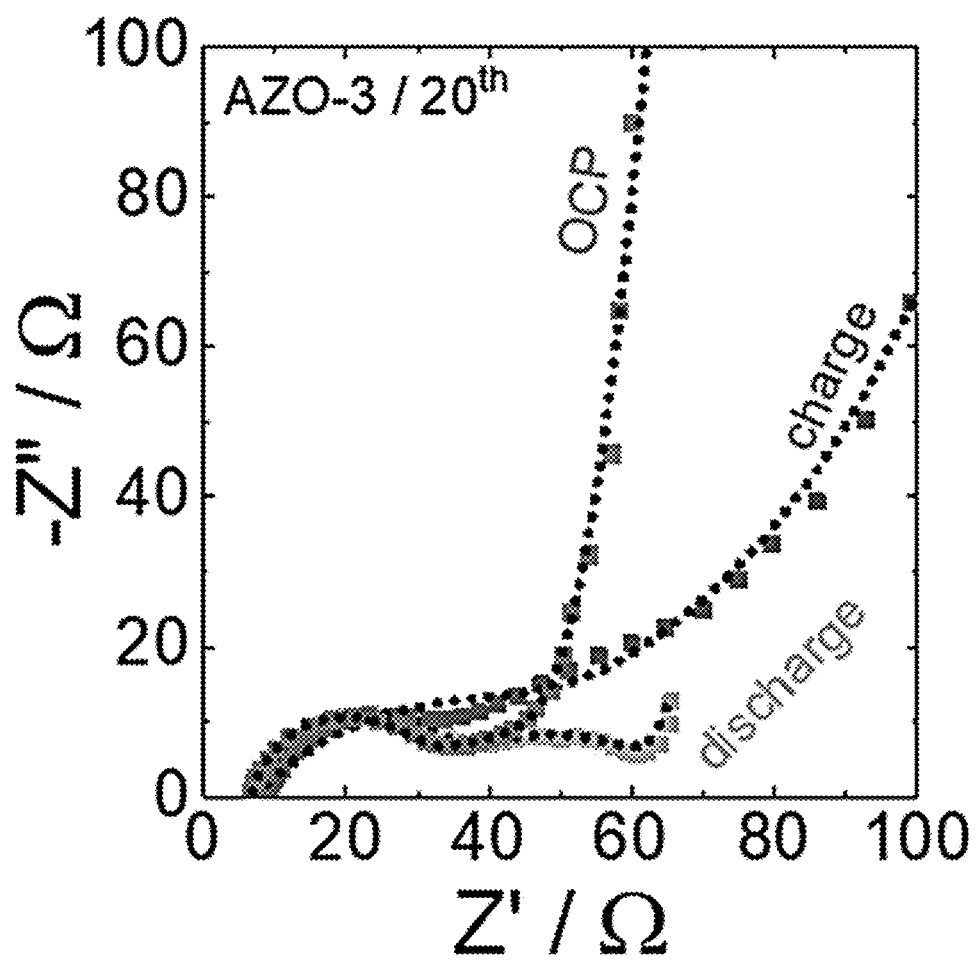

Electrochemical impedance spectroscopy (EIS) was used to analyze impedance for Example 2 (AZO-1), Comparative Example 3 (AZO-2), and Comparative Example 4 (AZO-3). Nyquist plots of Example 2 (AZO-1), Comparative Example 3 (AZO-2), and Comparative Example 4 (AZO-3) after performing 20 charge and discharge cycles at an open circuit potential (OCP) are shown in FIGS. 6A to 6C respectively. In the Nyquist plot, a single semicircle represents the resistance of the covalent organic framework, and a linear slope represents ion diffusion inside mesopores (Warburg impedance).

Referring to FIG. 6A, the charge transfer resistance (Rct) of Example 2 (AZO-1) after performing 20 discharge cycles was about 60 at charge and about 5Ω at discharge based on an equivalent circuit. A wetting process for cycling decreased Rct, and a solid electrolyte surface (SEI) stabilized an electrode surface. In addition, it was found that the electrode of Example 2 (AZO-1) was stable from a constant EIS curve for charge and discharge in FIG. 6A. In addition, a straight line having a 450 slope was shown after charging, and it was found therefrom that in the electrode of Example 2 (AZO-1), smooth Li$^+$ transport was performed by a mesoporous channel.

In contrast, referring to FIGS. 6B and 6C, Comparative Examples 3 (AZO-2) and Comparative Example 4 (AZO-3) formed a new semicircle in a low frequency range. The charge transfer resistance (Rct) of Comparative Example 3 (AZO-2) after performing 20 discharge cycles was about 400Ω at charge and about 61Ω at discharge based on an equivalent circuit. The charge transfer resistance (Rct) of Comparative Example 4 (AZO-3) was about 63Ω at charge and about 15Ω at discharge based on an equivalent circuit. From the above results, it was found that the covalent organic frameworks of Comparative Example 3 (AZO-2) and Comparative Example 4 (AZO-3) were decomposed and had poor impedance properties.

What is claimed is:

1. A covalent organic framework comprising a repeating unit represented by the following Chemical Formula 1:

[Chemical Formula 1]

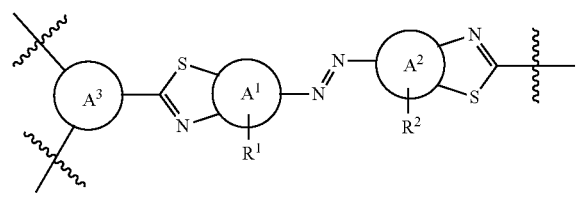

wherein

A$^1$, A$^2$, and A$^3$ are the same as or different from one another, and are independently of one another a monocyclic or polycyclic aromatic ring, and R$^1$ and R$^2$ are the same as or different from each other, and are independently of each other any one selected from hydrogen, a functional group containing at least one nitrogen, phosphorus, or sulfur, an unsubstituted or substituted C1-C6 alkyl group, an unsubstituted or substituted C2-C6 alkenyl group, an unsubstituted or substituted C2-C6 alkynyl group, and an unsubstituted or substituted C1-C6 alkoxy group.

2. The covalent organic framework of claim 1, wherein the covalent organic framework includes a hexagonal structure having one side formed by the repeating unit of Chemical Formula 1 and being provided with a pore inside.

3. The covalent organic framework of claim 2, wherein the pore has a diameter of 1.0 to 8.0 nm.

4. The covalent organic framework of claim 1, wherein the covalent organic framework includes a structure represented by the following Chemical Formula 2:

[Chemical Formula 2]

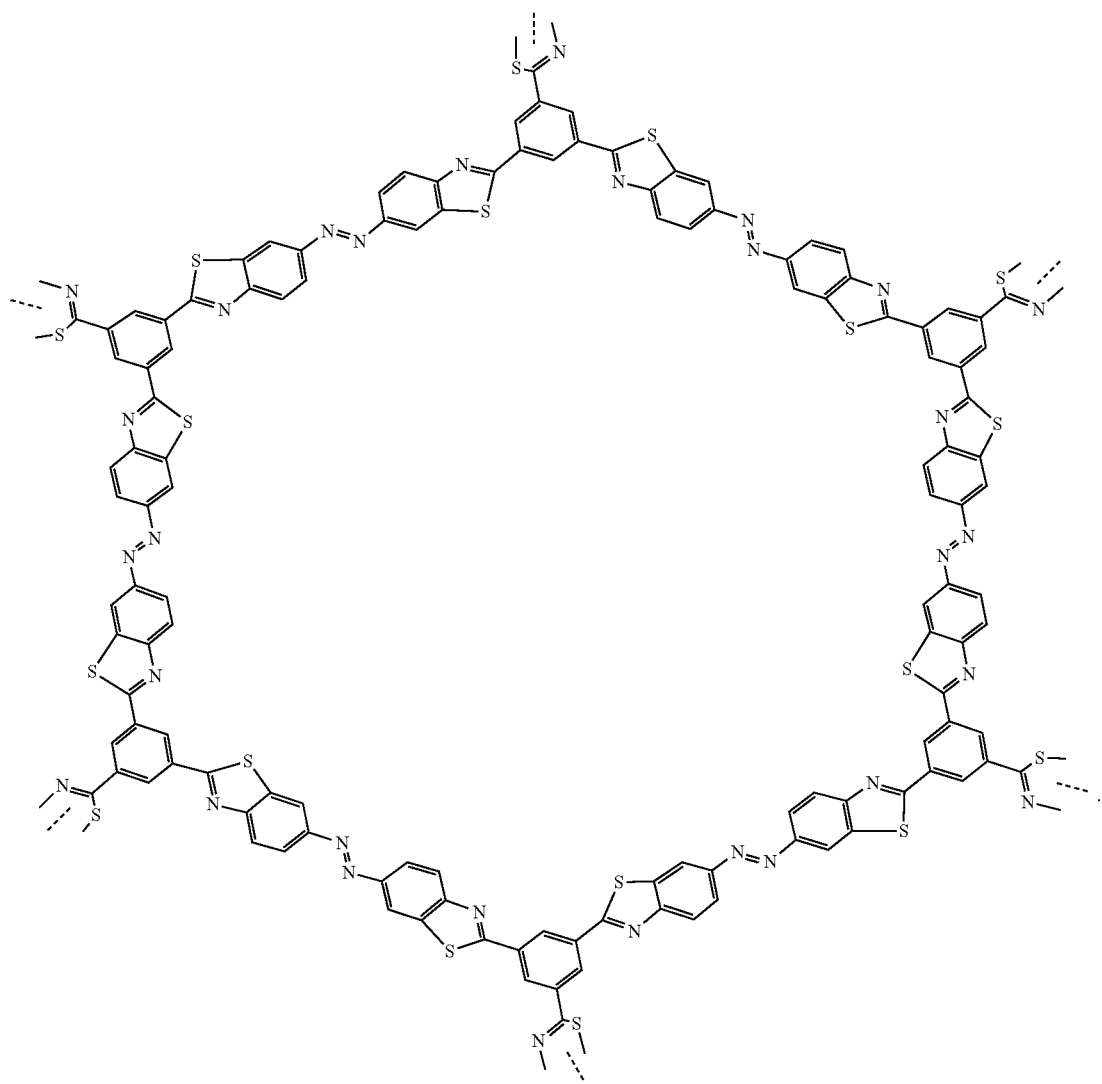

5. The covalent organic framework of claim 1, wherein the covalent organic framework includes a two-dimensional sheet in which the repeating unit of Chemical Formula 1 is horizontally arranged.

6. The covalent organic framework of claim 5, wherein the covalent organic framework includes a three-dimensional mesoporous framework in which a plurality of the sheets are vertically arranged in any one stacking mode selected from a staggered stacking mode, an alternating stacking mode, a unidirectional stacking mode, a random stacking mode, and an eclipsed stacking mode.

7. The covalent organic framework of claim 6, wherein a spacing between the vertically arranged sheets is 1.0 nm or less.

8. An electrode comprising the covalent organic framework of claim 1.

* * * * *